(12) United States Patent
Netzer et al.

(10) Patent No.: US 6,984,501 B1
(45) Date of Patent: Jan. 10, 2006

(54) VOLTAGE-GATED POTASSIUM CHANNEL AND ITS USE FOR DEVELOPMENT OF THERAPEUTICS

(75) Inventors: Rainer Netzer, Hamburg (DE); Olaf Pongs, Hamburg (DE)

(73) Assignee: Evotec Oai AG, Hamburg (DE)

( * ) Notice: Subject to any disclaimer, the term of this patent is extended or adjusted under 35 U.S.C. 154(b) by 0 days.

(21) Appl. No.: 09/762,278

(22) PCT Filed: Aug. 6, 1999

(86) PCT No.: PCT/EP99/05983

§ 371 (c)(1),
(2), (4) Date: Mar. 2, 2001

(87) PCT Pub. No.: WO00/08146

PCT Pub. Date: Feb. 17, 2000

(30) Foreign Application Priority Data

Aug. 6, 1998 (DE) .......................... 198 41 413

(51) Int. Cl.
| | |
|---|---|
| *C12P 21/06* | (2006.01) |
| *C07K 1/00* | (2006.01) |
| *C07H 21/04* | (2006.01) |
| *C12N 15/00* | (2006.01) |
| *C12N 1/20* | (2006.01) |

(52) U.S. Cl. ................ 435/69.1; 435/252.3; 435/320.1; 435/325; 435/471; 435/7.2; 530/350; 536/23.5

(58) Field of Classification Search ................ 530/350; 435/69.1, 70.1, 71.1, 71.2, 252.3, 320.1, 435/325, 471; 536/23.5
See application file for complete search history.

(56) References Cited

U.S. PATENT DOCUMENTS 5,710,019 A * 1/1998 Li et al.

OTHER PUBLICATIONS

The Ion Channel FactsBook, Voltage–Gated Channels, Conley & Brammar (Editors), pp. V–VII, XXXIX–XLIII, 524, 527, 528 and 555 (Academic Press 1999).*
Hwang PM et al. Journal of Neuroscience, 13:1569–1576, 1993.*
Ayala FJ and Kiger JA. Multiple Alleles. In Modern Genetics. The Benjamin/Cummings Publishing Co., Inc. Reading, Massachusetts. pp45–48, 1980.*
Rieger R, et al. Glossary of Genetics:Classical and Molecular. 5th ed. Springer–Verlag. New York. pp 16–17, 1991.*
Peale et al. Anal. Biochem. 256(2):158–168, 1998.*
Su et al. Biochem. Biophys. Res. Commum. 242:675–681, 1997.*
Zhu, "Structural and functional characterization of Kv6.2, a new gamma–subunit of voltage–gated potassium channel", Receptors and Channels, Bd. 6, 1999, Seiten 337–350.
"Shab–like voltage–gated potassium channel cKv6.2" Trembl Database Entry of 073606, Accession No. 073606, Aug. 1, 1998.
Peale et al, "Gallus gallus shab–like voltage–gated potassium channel cKv6.2 mRNA, complete cds", EMBL Database Entry U62139, Accession No. U62139, Mar. 23, 1998.

* cited by examiner

*Primary Examiner*—Robert S. Landsman
(74) *Attorney, Agent, or Firm*—Nixon & Vanderhye P.C.

(57) ABSTRACT

The invention relates to a novel tension-dependent potassium channel protein Kv6.2 (SEQ ID NO:1). The Kv6.2 gene is expressed preferably in the myocardium or in the hippocampus. Novel functional heteromultimeric potassium channels having high affinity with propafenone are formed in conjunction with subunit Kv2.1. According to the invention, said novel potassium channels are used in test systems which are suitable of identifying substances modulating, opening or closing the Kv2,1/Kv6.2 channels and which can be used as therapeutic agents.

25 Claims, 11 Drawing Sheets

*Figure 1B-1*

```
                ATGGAGCCGGCTCCTGGGGCACCCGGAGGCCCCGACG
hKv6.2
mKv6.2 hKv6.2          ATGGAGCCATGGCCCTGCTCCCCGGGGCGGCGGGACCCCGCCCGGACG        55
mKv6.2          CTGAACCTGGCAGCGCAGCCGACAGGGCC--T------C-----G--G--C----     165 hKv6.2          TCATCATCAACGTGGCGGCTGCCGCCCGTTGCCGCCCTGGCATGGCCGCTGCCGGATGCC  165
mKv6.2          --G--T------A--G-----T-----C----------C----T-- hKv6.2          CCCTCGCGCGCCTGGAGCGCCTGCCGCCTGCCGCGGCCACGACGACCTGCTGCGCGTGT   175
mKv6.2          T----G-------C--------AA--------GA-A-------------C- hKv6.2          GTGACGACTACGACGTGAGCCGCGACGAGTTCTTCTTCGACCGCAGCCCGTGCGCCTCC   235
mKv6.2          ---T-------------A-----------A-A------AG--------------T---G hKv6.2          GCGCCATCGTGGCGCTTTTGCGCGCAGGAAGCTGGACTGCTGCGGGCCCGTGCGGCGC   295
mKv6.2          --C--------GC----CC-C--AG--A-GG--------C-----T------C-- hKv6.2          TGGCCTTCCGCGACGAGCTGGCCTACTGGGGCATCGACGAGGCGCGCCTGGAGCGCTGCT  355
mKv6.2          -------------AA-AG--------------------AA----G----A----- hKv6.2          GCCTGCGCCGCCTGCCGCCGGCGGAGCCCGAGGAGGAGGCCGGCCCGAGGCCCGCGACGG  415
mKv6.2          -------------------C-----------------CC------A----C-C--A-C-C- hKv6.2          AGCGCGGGCGGCCCAGGGAGCCCGCGCGGCCGCGCCCTTCGGGGACCTTCGGGGGCTGCAGGCG  475
mKv6.2          CC--A---C------ACC-C---CCGC--A---------CA-C-------G--A-A- hKv6.2          GCCGGGCGGCCCTGCCGACGTGGTGGACAACCCGGACCTCGGGGCTGGCGGGCAAGCTCT  535
mKv6.2          --A-A---------T----A----------G----------C--------TCT-T- hKv6.2          TGCCCTGCCGCCTGCGCTCCGTTCCCTGCCCGTCACGACGCCGTGGCCTCTGCCTGAGCACGG  595
mKv6.2          -------A-AT--C-----G--T-------------------A------C---T--G-- hKv6.2          TGCCGGACATCCGCGCCGAGAGGGGGAGCGGAGTGCTCCCCAAGTGCCGCAGCCTGT    656
mKv6.2          -------TG-----A-----A------------------------A-A------A- hKv6.2          TCGTGCTGGAGACCGTGTGCGTTGCCTGGTTCTCCTTCGAGTTCCTGCTGCGCTCCTGC   715
mKv6.2          -----------------G----------------- hKv6.2          AGGCCGAGAGCAAGTGCGCCTTCCTGGCGCGCCACTCAACATCATTGACATCCTGGCGC  775
mKv6.2          ---T-------------------------C---GA----G--TGC-------C------CA
```

Figure 1B-2

```
hKv6.2  TCCTGCCGTTCTACGTGTCGCTGCTGCTGGGGCTGGCGGCAGCCCGGGGGGGACCAAGC  835
mKv6.2  ------------C--A-------------------CGC---A--------G--CACG--C-G--T--A hKv6.2  TCCTGGAGCGCGGGGGCTGGTGCTGCGGCTGCGTGCGCTGCGGCGTGCGCTGCTCTACGTGA  895
mKv6.2  -G--------------------T-----------------G----------------- hKv6.2  TGCGCCTGGCGGGCCACTCGCTGGGGCTGCGTTCGCTGGGCCTGACCATGCGCCGCTGCG  955
mKv6.2  ------------------T------------------C----T------C----G------ hKv6.2  CGCGCCAGTTCGGGCTGCTGCTGCTGTCCTCTGCGTGGCCATGGCGCTCTTCGGCCAC  1015
mKv6.2  ---------A-----------------C--------------------------G--- hKv6.2  TGGTGCACCTGGCCGAGCGAGCTGGGCGACCACCGTGGGCTACGGCGACATGGTCCCGCGCA  1075
mKv6.2  -C--------------T-------------T--A------------T--AG-----G--- hKv6.2  GCTATTGGTGGCCGTTCATCTCCACACCTTTTCGGCGCTCCTACTCCGAGTCAGGAGCAGC  1135
mKv6.2  ----C--------A----------------------C----------T--G------- hKv6.2  GCCTGCCCGGGTCAGTGGTGGCCAGCCCCGAGCCCTGCAGGAGGACAGCACGCACTCGGCCACAG  1195
mKv6.2  -----T--G--C------------G-----------------GC----------GTGAT-A--GTA hKv6.2  AGCAGCGCGCGGCGCAGCCTCCGCAGGGCCCCGACAGCCGGGCCTGGCCGACGACAACTCCGCCACAG  1315
mKv6.2  -A--------------------T--A------------GC----------GTGAT-A--GTA hKv6.2  CCACCGAGGACAGCTCGCAGGGCCCCGACAGCCGGGCCTGGCCGACGACAACTCCGCCGATG  1375
mKv6.2  -ACGTTC--C-----G-CACT--AGGA-AG-TCTCA--A--CT-AGAC--CAGG----CAhKv6.2  CG   CTGTGGTGGGGGCAGGGCGCTGA  1401
mKv6.2  G-AACT--CC--GC----TG--A-C----  1446
```

MEPWPCSPGGGGGTRARIIVIINVGGCRVRLAWAALARCPLARLERL 46

RACRGHDDLLRVCDDYDVSRDEFFEDRSPCAFRAIVALLRAGKLRLLRGPCALAFRDELA 106

YWGTDEARLEICCLRLLRRREEAAEARAGFTERGAQGSPARALGPRGRLQRGRRRLRDV 166
<u>PKC</u>

VDNPIISGLAGKLFACVSVSFVAVTAVGLCLSTMPDIRAEEERGECSPICRSL<u>FVLETVCV</u> 226
<u>S1</u>

AWFSFEFLLRSLQAESKCAFLRAPLNLIDILALLPFYVSLLLGLAAGFGGTKLLERAGLV 286
<u>S2</u>                                       <u>S3</u>

<u>LRLLRALRVLYVMR</u>LARIISLGLRSLGLTMRRCAREFGLLLL<u>FLCVAMALFAPLVILA</u>ERE 346
<u>S4</u>                 <u>PKC</u>               <u>S5</u>

LGARRDFSSVPASYWWAVISMTTVGYGDMVPRSLPGQVVALSSIL<u>SGILLMAFPVTSIFH</u> 406
                                              <u>S6</u>

TFSR<u>SYSEL</u>KEQQQRAASPEPALQEDSTIISATATEDSSQGPDSAGLADDSADALWVRAGR 466
<u>CamK</u>                                                <u>CamK</u>

Figure 1C

| % | rKv6.1 | rKv1.4 | rKv2.1 | rKv3.1 | rKv4.2 | rKv5.1 | rKv8.1 |
|---|---|---|---|---|---|---|---|
| hKv6.2 | 62.0 | 35.2 | 39.2 | 38.0 | 34.0 | 34.0 | 38.8 |

Figure 1D

SEQUENCE LISTING

<160> NUMBER OF SEQ ID NOS: 28

<210> SEQ ID NO 1
<211> LENGTH: 1401
<212> TYPE: DNA
<213> ORGANISM: Homo sapiens
<220> FEATURE:
<221> NAME/KEY: CDS
<222> LOCATION: (1)..(1401)
<223> OTHER INFORMATION: Mature human Kv6.2 protein

<400> SEQUENCE: 1

```
atg gag cca tgg ccc tgc tcc ccg ggc ggc ggc ggg acc cgc gcc       48
Met Glu Pro Trp Pro Cys Ser Pro Gly Gly Gly Gly Gly Thr Arg Ala
 1               5                  10                  15 cgg cac gtc atc atc aac gtg ggc ggc tgc cgc gtg cgc ctg gca tgg   96
Arg His Val Ile Ile Asn Val Gly Gly Cys Arg Val Arg Leu Ala Trp
                20                  25                  30 gcc gcg ctg gcg cga tgc ccc ctc gcg cgc ctg gag cgc ctg cgc gcc  144
Ala Ala Leu Ala Arg Cys Pro Leu Ala Arg Leu Glu Arg Leu Arg Ala
             35                  40                  45 tgc cgc ggc cac gac gac ctg ctg cgc gtg tgt gac gac tac gac gtg  192
Cys Arg Gly His Asp Asp Leu Leu Arg Val Cys Asp Asp Tyr Asp Val
 50                  55                  60 agc cgc gac gag ttc ttc ttc gac cgc agc ccg tgc gcc ttc cgc gcc  240
Ser Arg Asp Glu Phe Phe Phe Asp Arg Ser Pro Cys Ala Phe Arg Ala
 65                  70                  75                  80 atc gtg gcg ctt ttg cgc gca ggg aag ctg cga ctg ctg cgg ggc ccg  288
Ile Val Ala Leu Leu Arg Ala Gly Lys Leu Arg Leu Leu Arg Gly Pro
                 85                  90                  95 tgc gcg ctg gcc ttc cgc gac gag ctg gcc tac tgg ggc atc gac gag  336
Cys Ala Leu Ala Phe Arg Asp Glu Leu Ala Tyr Trp Gly Ile Asp Glu
            100                 105                 110 gcg cgc ctg gag cgc tgc tgc ctg cgc cgc ctg cgc cgc gag gag      384
Ala Arg Leu Glu Arg Cys Cys Leu Arg Arg Leu Arg Arg Arg Glu Glu
        115                 120                 125 gag gcg gcc gag gcc cgc gcg ggg ccg acg gag cgc ggg gcg cag ggg  432
Glu Ala Ala Glu Ala Arg Ala Gly Pro Thr Glu Arg Gly Ala Gln Gly
    130                 135                 140 agc ccg gcg cgc gcc ctg gga cct cgg ggg cgg ctg cag cgc ggc cgg  480
Ser Pro Ala Arg Ala Leu Gly Pro Arg Gly Arg Leu Gln Arg Gly Arg
145                 150                 155                 160
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| cgg | cgc | ctg | cgc | gac | gtg | gtg | gac | aac | ccg | cac | tcg | ggg | ctg | gcg | ggc | 528  |
| Arg | Arg | Leu | Arg | Asp | Val | Val | Asp | Asn | Pro | His | Ser | Gly | Leu | Ala | Gly |      |
|     |     |     |     | 165 |     |     |     |     | 170 |     |     |     |     | 175 |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| aag | ctc | ttc | gcc | tgc | gtg | tcc | gtg | tcc | ttc | gtg | gcc | gtc | acg | gcc | gtg | 576  |
| Lys | Leu | Phe | Ala | Cys | Val | Ser | Val | Ser | Phe | Val | Ala | Val | Thr | Ala | Val |      |
|     |     |     | 180 |     |     |     |     | 185 |     |     |     |     | 190 |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ggc | ctc | tgc | ctg | agc | acc | atg | ccg | gac | atc | cgc | gcc | gag | gag | gag | cgg | 624  |
| Gly | Leu | Cys | Leu | Ser | Thr | Met | Pro | Asp | Ile | Arg | Ala | Glu | Glu | Glu | Arg |      |
|     |     | 195 |     |     |     |     | 200 |     |     |     |     | 205 |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ggc | gag | tgc | tcc | ccc | aag | tgc | cgc | agc | ctg | ttc | gtg | ctg | gag | acc | gtg | 672  |
| Gly | Glu | Cys | Ser | Pro | Lys | Cys | Arg | Ser | Leu | Phe | Val | Leu | Glu | Thr | Val |      |
|     | 210 |     |     |     |     |     | 215 |     |     |     |     | 220 |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| tgc | gtg | gcc | tgg | ttc | tcc | ttc | gag | ttc | ctg | ctg | cgc | tcc | ctg | cag | gcc | 720  |
| Cys | Val | Ala | Trp | Phe | Ser | Phe | Glu | Phe | Leu | Leu | Arg | Ser | Leu | Gln | Ala |      |
| 225 |     |     |     |     | 230 |     |     |     |     | 235 |     |     |     |     | 240 |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gag | agc | aag | tgc | gcc | ttc | ctg | cgc | gcg | cca | ctc | aac | atc | att | gac | atc | 768  |
| Glu | Ser | Lys | Cys | Ala | Phe | Leu | Arg | Ala | Pro | Leu | Asn | Ile | Ile | Asp | Ile |      |
|     |     |     | 245 |     |     |     |     | 250 |     |     |     |     | 255 |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ctg | gcg | ctc | ctg | ccg | ttc | tac | gtg | tcg | ctg | ctg | ggg | ctg | gcg | gca | 816  |     |
| Leu | Ala | Leu | Leu | Pro | Phe | Tyr | Val | Ser | Leu | Leu | Gly | Leu | Ala | Ala |      |     |
|     |     | 260 |     |     |     |     | 265 |     |     |     |     | 270 |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ggc | ccg | ggc | ggg | acc | aag | ctc | ctg | gag | cgc | gcg | ggg | ctg | gtg | ctg | cgg | 864  |
| Gly | Pro | Gly | Gly | Thr | Lys | Leu | Leu | Glu | Arg | Ala | Gly | Leu | Val | Leu | Arg |      |
|     | 275 |     |     |     |     |     | 280 |     |     |     |     | 285 |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ctg | ctg | cgt | gcg | ctg | cgc | gtg | ctc | tac | gtg | atg | cgc | ctg | gcg | cgc | cac | 912  |
| Leu | Leu | Arg | Ala | Leu | Arg | Val | Leu | Tyr | Val | Met | Arg | Leu | Ala | Arg | His |      |
| 290 |     |     |     |     | 295 |     |     |     |     | 300 |     |     |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| tcg | ctg | ggg | ctg | cgt | tcg | ctg | ggc | ctg | acc | atg | cgc | cgc | tgc | gcg | cgc | 960  |
| Ser | Leu | Gly | Leu | Arg | Ser | Leu | Gly | Leu | Thr | Met | Arg | Arg | Cys | Ala | Arg |      |
| 305 |     |     |     |     | 310 |     |     |     |     | 315 |     |     |     |     | 320 |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gag | ttc | ggg | ctg | ctg | ctg | ctg | ttc | ctc | tgc | gtg | gcc | atg | gcg | ctc | ttc | 1008 |
| Glu | Phe | Gly | Leu | Leu | Leu | Leu | Phe | Leu | Cys | Val | Ala | Met | Ala | Leu | Phe |      |
|     |     |     |     | 325 |     |     |     |     | 330 |     |     |     |     | 335 |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gcg | cca | ctg | gtg | cac | ctg | gcc | gag | cgc | gag | ctg | ggc | gcg | cgc | cgc | gac | 1056 |
| Ala | Pro | Leu | Val | His | Leu | Ala | Glu | Arg | Glu | Leu | Gly | Ala | Arg | Arg | Asp |      |
|     |     |     | 340 |     |     |     |     | 345 |     |     |     |     | 350 |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ttc | tcc | agc | gtg | ccc | gcc | agc | tat | tgg | tgg | gcc | gtc | atc | tcc | atg | acc | 1104 |
| Phe | Ser | Ser | Val | Pro | Ala | Ser | Tyr | Trp | Trp | Ala | Val | Ile | Ser | Met | Thr |      |
|     |     | 355 |     |     |     |     | 360 |     |     |     |     | 365 |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| acc | gtg | ggc | tac | ggc | gac | atg | gtc | ccg | cgc | agc | ctg | ccc | ggg | cag | gtg | 1152 |
| Thr | Val | Gly | Tyr | Gly | Asp | Met | Val | Pro | Arg | Ser | Leu | Pro | Gly | Gln | Val |      |
|     | 370 |     |     |     |     | 375 |     |     |     |     | 380 |     |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gtg | gcg | ctc | agc | agc | atc | ctc | agc | ggc | atc | ctg | ctc | atg | gcc | ttc | ccg | 1200 |
| Val | Ala | Leu | Ser | Ser | Ile | Leu | Ser | Gly | Ile | Leu | Leu | Met | Ala | Phe | Pro |      |
| 385 |     |     |     |     | 390 |     |     |     |     | 395 |     |     |     |     | 400 |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gtc | acc | tcc | atc | ttc | cac | acc | ttt | tcg | cgc | tcc | tac | tcc | gag | ctc | aag | 1248 |
| Val | Thr | Ser | Ile | Phe | His | Thr | Phe | Ser | Arg | Ser | Tyr | Ser | Glu | Leu | Lys |      |
|     |     |     |     | 405 |     |     |     |     | 410 |     |     |     |     | 415 |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| gag | cag | cag | cag | cgc | gcg | gcc | agc | ccc | gag | ccg | gcc | ctg | cag | gag | gac | 1296 |
| Glu | Gln | Gln | Gln | Arg | Ala | Ala | Ser | Pro | Glu | Pro | Ala | Leu | Gln | Glu | Asp |      |
|     |     |     | 420 |     |     |     |     | 425 |     |     |     |     | 430 |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| agc | acg | cac | tcg | gcc | aca | gcc | acc | gag | gac | agc | tcg | cag | ggc | ccc | gac | 1344 |
| Ser | Thr | His | Ser | Ala | Thr | Ala | Thr | Glu | Asp | Ser | Ser | Gln | Gly | Pro | Asp |      |
|     |     | 435 |     |     |     |     | 440 |     |     |     |     | 445 |     |     |     |      |

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| agc | gcg | ggc | ctg | gcc | gac | gac | tcc | gcg | gat | gcg | ctg | tgg | gtg | cgg | gca | 1392 |
| Ser | Ala | Gly | Leu | Ala | Asp | Asp | Ser | Ala | Asp | Ala | Leu | Trp | Val | Arg | Ala |      |
|     | 450 |     |     |     |     | 455 |     |     |     |     | 460 |     |     |     |     |      |

|     |     |      |
|-----|-----|------|
| ggg | cgc | tga  |
| Gly | Arg |      |
|     |     | 1401 |

465

<210> SEQ ID NO 2
<211> LENGTH: 466
<212> TYPE: PRT
<213> ORGANISM: Homo sapiens

<400> SEQUENCE: 2

```
Met Glu Pro Trp Pro Cys Ser Pro Gly Gly Gly Gly Thr Arg Ala
 1               5                  10                  15

Arg His Val Ile Ile Asn Val Gly Gly Cys Arg Val Arg Leu Ala Trp
                 20                  25                  30

Ala Ala Leu Ala Arg Cys Pro Leu Ala Arg Leu Glu Arg Leu Arg Ala
             35                  40                  45

Cys Arg Gly His Asp Asp Leu Leu Arg Val Cys Asp Asp Tyr Asp Val
         50                  55                  60

Ser Arg Asp Glu Phe Phe Phe Asp Arg Ser Pro Cys Ala Phe Arg Ala
 65                  70                  75                  80

Ile Val Ala Leu Leu Arg Ala Gly Lys Leu Arg Leu Leu Arg Gly Pro
                 85                  90                  95

Cys Ala Leu Ala Phe Arg Asp Glu Leu Ala Tyr Trp Gly Ile Asp Glu
            100                 105                 110

Ala Arg Leu Glu Arg Cys Cys Leu Arg Arg Leu Arg Arg Arg Glu Glu
            115                 120                 125

Glu Ala Ala Glu Ala Arg Ala Gly Pro Thr Glu Arg Gly Ala Gln Gly
        130                 135                 140

Ser Pro Ala Arg Ala Leu Gly Pro Arg Gly Arg Leu Gln Arg Gly Arg
145                 150                 155                 160

Arg Arg Leu Arg Asp Val Val Asp Asn Pro His Ser Gly Leu Ala Gly
                165                 170                 175

Lys Leu Phe Ala Cys Val Ser Val Ser Phe Val Ala Val Thr Ala Val
            180                 185                 190

Gly Leu Cys Leu Ser Thr Met Pro Asp Ile Arg Ala Glu Glu Glu Arg
            195                 200                 205

Gly Glu Cys Ser Pro Lys Cys Arg Ser Leu Phe Val Leu Glu Thr Val
        210                 215                 220

Cys Val Ala Trp Phe Ser Phe Glu Phe Leu Leu Arg Ser Leu Gln Ala
225                 230                 235                 240

Glu Ser Lys Cys Ala Phe Leu Arg Ala Pro Leu Asn Ile Ile Asp Ile
                245                 250                 255

Leu Ala Leu Leu Pro Phe Tyr Val Ser Leu Leu Gly Leu Ala Ala
            260                 265                 270

Gly Pro Gly Gly Thr Lys Leu Leu Glu Arg Ala Gly Leu Val Leu Arg
            275                 280                 285

Leu Leu Arg Ala Leu Arg Val Leu Tyr Val Met Arg Leu Ala Arg His
        290                 295                 300

Ser Leu Gly Leu Arg Ser Leu Gly Leu Thr Met Arg Arg Cys Ala Arg
305                 310                 315                 320

Glu Phe Gly Leu Leu Leu Leu Phe Leu Cys Val Ala Met Ala Leu Phe
                325                 330                 335

Ala Pro Leu Val His Leu Ala Glu Glu Leu Gly Ala Arg Arg Asp
            340                 345                 350

Phe Ser Ser Val Pro Ala Ser Tyr Trp Trp Ala Val Ile Ser Met Thr
        355                 360                 365
```

-continued

```
Thr Val Gly Tyr Gly Asp Met Val Pro Arg Ser Leu Pro Gly Gln Val
    370             375                 380
Val Ala Leu Ser Ser Ile Leu Ser Gly Ile Leu Leu Met Ala Phe Pro
385                 390                 395                 400
Val Thr Ser Ile Phe His Thr Phe Ser Arg Ser Tyr Ser Glu Leu Lys
                405                 410                 415
Glu Gln Gln Gln Arg Ala Ala Ser Pro Glu Pro Ala Leu Gln Glu Asp
            420                 425                 430
Ser Thr His Ser Ala Thr Ala Thr Glu Asp Ser Ser Gln Gly Pro Asp
            435                 440                 445
Ser Ala Gly Leu Ala Asp Asp Ser Ala Asp Ala Leu Trp Val Arg Ala
    450                 455                 460
Gly Arg
465
```

<210> SEQ ID NO 3
<211> LENGTH: 1446
<212> TYPE: DNA
<213> ORGANISM: Mouse
<220> FEATURE:
<221> NAME/KEY: CDS
<222> LOCATION: (1)..(1446)
<223> OTHER INFORMATION: mature murine Kv6.2 protein

<400> SEQUENCE: 3

```
atg gcc cgg ctc ctg ggg cac ccg gag gcc ccc gac gcg gaa cct ggc      48
Met Ala Arg Leu Leu Gly His Pro Glu Ala Pro Asp Ala Glu Pro Gly
  1               5                  10                  15 agc gca ggc cga cag ggc cgt ggc ggc cgc ggg gcc cgg gcg cgc cac      96
Ser Ala Gly Arg Gln Gly Arg Gly Gly Arg Gly Ala Arg Ala Arg His
             20                  25                  30 gtc gtt atc aac atc tgg ggc tgc agg gtg cgt ctg gcc tgg gcc gcg     144
Val Val Ile Asn Ile Trp Gly Cys Arg Val Arg Leu Ala Trp Ala Ala
         35                  40                  45 ctg gcc cgc tgt ctc ctg gcg cgc ctc gag cgc ctg cga acc tgc cgc     192
Leu Ala Arg Cys Leu Leu Ala Arg Leu Glu Arg Leu Arg Thr Cys Arg
     50                  55                  60 ggc cac gag aaa ctg ctg cgc gtg tgt tac gac tac gac atg agc cgc     240
Gly His Glu Lys Leu Leu Arg Val Cys Tyr Asp Tyr Asp Met Ser Arg
 65                  70                  75                  80 gac aaa ttc ttc ttc gaa ggc agc ccg tgc gct ttc ggc ccc atc gtg     288
Asp Lys Phe Phe Phe Glu Gly Ser Pro Cys Ala Phe Gly Pro Ile Val
                 85                  90                  95 gcg ctg ctg cgc gcc cgc aaa gtg agg gtg ctg cgc ggc cct tgc gcc     336
Ala Leu Leu Arg Ala Arg Lys Val Arg Val Leu Arg Gly Pro Cys Ala
            100                 105                 110 ctg gcc ttc cgc gaa aaa gtg gcc tac tgg ggc atc gac gaa acg cgg     384
Leu Ala Phe Arg Glu Lys Val Ala Tyr Trp Gly Ile Asp Glu Thr Arg
        115                 120                 125 ctg gaa cgc tgc tgc ctg cgc cgc ctg cgc cgc cgc gag gag gag gcc     432
Leu Glu Arg Cys Cys Leu Arg Arg Leu Arg Arg Arg Glu Glu Glu Ala
    130                 135                 140 ccc gag gcc agc gcc gcg cag ccc gcc cga ggg ccg cag acc acc ccc     480
Pro Glu Ala Ser Ala Ala Gln Pro Ala Arg Gly Pro Gln Thr Thr Pro
145                 150                 155                 160 cgc cga gcc ctg gga ccc agc ggg cgg ctg gag aga ggc aga cgg cgc     528
Arg Arg Ala Leu Gly Pro Ser Gly Arg Leu Glu Arg Gly Arg Arg Arg
                165                 170                 175 ttg cga gac gtg gtg gag aac ccg cac tcc ggg ctg gcg ggc atc ttt     576
Leu Arg Asp Val Val Glu Asn Pro His Ser Gly Leu Ala Gly Ile Phe
```

|     |     |
| --- | --- |
| ttc gca tat gtc tcc gtg gct ttc gtg gcc gtc aca gcc gtc ggc ttg<br>Phe Ala Tyr Val Ser Val Ala Phe Val Ala Val Thr Ala Val Gly Leu<br>        195                     200                   205 | 624 |
| tgc ctg agc acc atg ccg gat gtc cgc gca gaa gag gaa cgg ggc gag<br>Cys Leu Ser Thr Met Pro Asp Val Arg Ala Glu Glu Glu Arg Gly Glu<br>    210                    215                   220 | 672 |
| tgc tcc aca aag tgc cgc aac ctg ttc gtg ctg gag acg gtg tgc gtg<br>Cys Ser Thr Lys Cys Arg Asn Leu Phe Val Leu Glu Thr Val Cys Val<br>225                    230                   235                   240 | 720 |
| gcc tgg ttc tcc ttc gag ttc ctg ctg cgc tcc ctg cag gct gag agc<br>Ala Trp Phe Ser Phe Glu Phe Leu Leu Arg Ser Leu Gln Ala Glu Ser<br>                245                   250                   255 | 768 |
| aag tgc gcc ttc ctc cgg acg ccg ctt gcc atc atc gac atc ctg gcc<br>Lys Cys Ala Phe Leu Arg Thr Pro Leu Ala Ile Ile Asp Ile Leu Ala<br>              260                   265                   270 | 816 |
| atc ctg ccc tta tac gtg tcg ctc gcg gga ctg gcg gca ggg ccc<br>Ile Leu Pro Leu Tyr Val Ser Leu Leu Ala Gly Leu Ala Ala Gly Pro<br>        275                    280                   285 | 864 |
| acg ggc agc aag atg ctg gag cgc gcg ggt ctg gtg ctg cgg ctg ctg<br>Thr Gly Ser Lys Met Leu Glu Arg Ala Gly Leu Val Leu Arg Leu Leu<br>    290                    295                   300 | 912 |
| cgg gcg ctg cgc gtg ctc tac gtg atg cgc ctg gcg cgc cac tcg ttg<br>Arg Ala Leu Arg Val Leu Tyr Val Met Arg Leu Ala Arg His Ser Leu<br>305                    310                   315                   320 | 960 |
| ggg ctg cgc tcg ctt ggc ctc acc gtg cgc cgc tgc gcg cgc gag ttc<br>Gly Leu Arg Ser Leu Gly Leu Thr Val Arg Arg Cys Ala Arg Glu Phe<br>                325                   330                   335 | 1008 |
| gga ctg ctg ctg ctc ttc ctc tgc gtg gcc atg gcg ctc ttc gcg ccg<br>Gly Leu Leu Leu Leu Phe Leu Cys Val Ala Met Ala Leu Phe Ala Pro<br>              340                   345                   350 | 1056 |
| ctc gtg cac ctg gct gag cgc gag ctg ggc gct cac cgc gac ttc tcc<br>Leu Val His Leu Ala Glu Arg Glu Leu Gly Ala His Arg Asp Phe Ser<br>        355                    360                   365 | 1104 |
| agc gtc ccc gcc agc tac tgg tgg gca gtc atc tcc atg acc acc gtg<br>Ser Val Pro Ala Ser Tyr Trp Trp Ala Val Ile Ser Met Thr Thr Val<br>    370                    375                   380 | 1152 |
| ggc tat gga gac atg gtg ccg cgc agc ctt ccg ggc cag gtg gtg gcg<br>Gly Tyr Gly Asp Met Val Pro Arg Ser Leu Pro Gly Gln Val Val Ala<br>385                    390                   395                   400 | 1200 |
| ctg agc agc atc ctc agc ggc atc ctc ctc atg gcc ttc cct gtc acc<br>Leu Ser Ser Ile Leu Ser Gly Ile Leu Leu Met Ala Phe Pro Val Thr<br>                405                   410                   415 | 1248 |
| tcc atc ttc cac acc ttc tcg cgc tcc tat tcg gag ctc aag gag cag<br>Ser Ile Phe His Thr Phe Ser Arg Ser Tyr Ser Glu Leu Lys Glu Gln<br>              420                   425                   430 | 1296 |
| caa cag cgc gcg gcc agc cct gaa ccg gcc ctg cgc gag gac agc acg<br>Gln Gln Arg Ala Ala Ser Pro Glu Pro Ala Leu Arg Glu Asp Ser Thr<br>        435                    440                   445 | 1344 |
| cgt gat gac agt aca cgt tcg gcc agc gcc act gag gac agc tct cag<br>Arg Asp Asp Ser Thr Arg Ser Ala Ser Ala Thr Glu Asp Ser Ser Gln<br>450                    455                   460 | 1392 |
| gac cct gag acc gca ggc gcg gca ggg aac ttg ccg ggc cgg gtg gga<br>Asp Pro Glu Thr Ala Gly Ala Ala Gly Asn Leu Pro Gly Arg Val Gly<br>465                    470                   475                   480 | 1440 |
| ccc tga<br>Pro | 1446 |

<210> SEQ ID NO 4

<211> LENGTH: 481
<212> TYPE: PRT
<213> ORGANISM: Mouse

<400> SEQUENCE: 4

```
Met Ala Arg Leu Leu Gly His Pro Glu Ala Pro Asp Ala Glu Pro Gly
 1               5                   10                  15

Ser Ala Gly Arg Gln Gly Arg Gly Arg Gly Ala Arg Ala Arg His
            20                  25                  30

Val Val Ile Asn Ile Trp Gly Cys Arg Val Arg Leu Ala Trp Ala Ala
        35                  40                  45

Leu Ala Arg Cys Leu Leu Ala Arg Leu Glu Arg Leu Arg Thr Cys Arg
    50                  55                  60

Gly His Glu Lys Leu Leu Arg Val Cys Tyr Asp Tyr Asp Met Ser Arg
 65                  70                  75                  80

Asp Lys Phe Phe Phe Glu Gly Ser Pro Cys Ala Phe Gly Pro Ile Val
                85                  90                  95

Ala Leu Leu Arg Ala Arg Lys Val Arg Val Leu Arg Gly Pro Cys Ala
            100                 105                 110

Leu Ala Phe Arg Glu Lys Val Ala Tyr Trp Gly Ile Asp Glu Thr Arg
        115                 120                 125

Leu Glu Arg Cys Cys Leu Arg Arg Leu Arg Arg Glu Glu Glu Ala
    130                 135                 140

Pro Glu Ala Ser Ala Ala Gln Pro Ala Arg Gly Pro Gln Thr Thr Pro
145                 150                 155                 160

Arg Arg Ala Leu Gly Pro Ser Gly Arg Leu Glu Arg Gly Arg Arg Arg
                165                 170                 175

Leu Arg Asp Val Val Glu Asn Pro His Ser Gly Leu Ala Gly Ile Phe
            180                 185                 190

Phe Ala Tyr Val Ser Val Ala Phe Val Ala Val Thr Ala Val Gly Leu
        195                 200                 205

Cys Leu Ser Thr Met Pro Asp Val Arg Ala Glu Glu Arg Gly Glu
    210                 215                 220

Cys Ser Thr Lys Cys Arg Asn Leu Phe Val Leu Glu Thr Val Cys Val
225                 230                 235                 240

Ala Trp Phe Ser Phe Glu Phe Leu Leu Arg Ser Leu Gln Ala Glu Ser
                245                 250                 255

Lys Cys Ala Phe Leu Arg Thr Pro Leu Ala Ile Ile Asp Ile Leu Ala
            260                 265                 270

Ile Leu Pro Leu Tyr Val Ser Leu Leu Ala Gly Leu Ala Ala Gly Pro
        275                 280                 285

Thr Gly Ser Lys Met Leu Glu Arg Ala Gly Leu Val Leu Arg Leu Leu
    290                 295                 300

Arg Ala Leu Arg Val Leu Tyr Val Met Arg Leu Ala Arg His Ser Leu
305                 310                 315                 320

Gly Leu Arg Ser Leu Gly Leu Thr Val Arg Cys Ala Arg Glu Phe
                325                 330                 335

Gly Leu Leu Leu Phe Leu Cys Val Ala Met Ala Leu Phe Ala Pro
            340                 345                 350

Leu Val His Leu Ala Glu Arg Glu Leu Gly Ala His Arg Asp Phe Ser
        355                 360                 365

Ser Val Pro Ala Ser Tyr Trp Trp Ala Val Ile Ser Met Thr Thr Val
    370                 375                 380

Gly Tyr Gly Asp Met Val Pro Arg Ser Leu Pro Gly Gln Val Val Ala
```

-continued

```
            385                 390                 395                 400
Leu Ser Ser Ile Leu Ser Gly Ile Leu Leu Met Ala Phe Pro Val Thr
                405                 410                 415

Ser Ile Phe His Thr Phe Ser Arg Ser Tyr Ser Glu Leu Lys Glu Gln
            420                 425                 430

Gln Gln Arg Ala Ala Ser Pro Glu Pro Ala Leu Arg Glu Asp Ser Thr
            435                 440                 445

Arg Asp Asp Ser Thr Arg Ser Ala Ser Ala Thr Glu Asp Ser Ser Gln
        450                 455                 460

Asp Pro Glu Thr Ala Gly Ala Ala Gly Asn Leu Pro Gly Arg Val Gly
465                 470                 475                 480

Pro

<210> SEQ ID NO 5
<211> LENGTH: 620
<212> TYPE: DNA
<213> ORGANISM: Homo sapiens
<220> FEATURE:
<221> NAME/KEY: CDS
<222> LOCATION: (150)..(620)
<223> OTHER INFORMATION: coding region of the human genomic
      SacI/PstI fragment

<400> SEQUENCE: 5
gagctcacct ccgagggttc ggtgccggcc cggcccctgg atcccgcgg gcggacgcgc      60 tcccccagct cagccctcgc gaccctaacg cggtccgttc cttttgcagg agccgggcag    120
gagcccctcg gtccggtccg gccctgcgc atg gag cca tgg ccc tgc tcc ccg      173
                                Met Glu Pro Trp Pro Cys Ser Pro
                                  1               5 ggc ggc ggc ggc ggg acc cgc gcc cgg cac gtc atc atc aac gtg ggc      221
Gly Gly Gly Gly Gly Thr Arg Ala Arg His Val Ile Ile Asn Val Gly
         10                  15                  20 ggc tgc cgc gtg cgc ctg gca tgg gcc gcg ctg gcg cga tgc ccc ctc      269
Gly Cys Arg Val Arg Leu Ala Trp Ala Ala Leu Ala Arg Cys Pro Leu
 25                  30                  35                  40 gcg cgc ctg gag cgc ctg cgc gcc tgc cgc ggc cac gac gac ctg ctg      317
Ala Arg Leu Glu Arg Leu Arg Ala Cys Arg Gly His Asp Asp Leu Leu
                 45                  50                  55 cgc gtg tgt gac gac tac gac gtg agc cgc gac gag ttc ttc ttc gac      365
Arg Val Cys Asp Asp Tyr Asp Val Ser Arg Asp Glu Phe Phe Phe Asp
             60                  65                  70 cgc agc ccg tgc gcc ttc cgc gcc atc gtg gcg ctt ttg cgc gca ggg      413
Arg Ser Pro Cys Ala Phe Arg Ala Ile Val Ala Leu Leu Arg Ala Gly
         75                  80                  85 aag ctg cga ctg ctg cgg ggc ccg tgc gcg ctg gcc ttc cga gac gag      461
Lys Leu Arg Leu Leu Arg Gly Pro Cys Ala Leu Ala Phe Arg Asp Glu
 90                  95                 100 ctg gcc tac tgg ggc atc gac gag gcg cgc atg gac tgc cgc tgc ctg      509
Leu Ala Tyr Trp Gly Ile Asp Glu Ala Arg Met Asp Cys Arg Cys Leu
105                 110                 115                 120 cgc cgc atg cgc cgc cgc gag gag gag gcg gcc gag gcc cgc gcg ggg      557
Arg Arg Met Arg Arg Arg Glu Glu Glu Ala Ala Glu Ala Arg Ala Gly
                125                 130                 135 ccg acg gag cgc ggg gcg cag ggg agc ccg gcg cgc gcc ctg gga cct      605
Pro Thr Glu Arg Gly Ala Gln Gly Ser Pro Ala Arg Ala Leu Gly Pro
            140                 145                 150 cgg ggg cgg ctg cag                                                  620
Arg Gly Arg Leu Gln
            155
```

<210> SEQ ID NO 6
<211> LENGTH: 157
<212> TYPE: PRT
<213> ORGANISM: Homo sapiens

<400> SEQUENCE: 6

```
Met Glu Pro Trp Pro Cys Ser Pro Gly Gly Gly Gly Thr Arg Ala
 1               5                  10                  15

Arg His Val Ile Ile Asn Val Gly Gly Cys Arg Val Arg Leu Ala Trp
                20                  25                  30

Ala Ala Leu Ala Arg Cys Pro Leu Ala Arg Leu Glu Arg Leu Arg Ala
             35                  40                  45

Cys Arg Gly His Asp Asp Leu Leu Arg Val Cys Asp Asp Tyr Asp Val
         50                  55                  60

Ser Arg Asp Glu Phe Phe Phe Asp Arg Ser Pro Cys Ala Phe Arg Ala
 65                  70                  75                  80

Ile Val Ala Leu Leu Arg Ala Gly Lys Leu Arg Leu Leu Arg Gly Pro
                 85                  90                  95

Cys Ala Leu Ala Phe Arg Asp Glu Leu Ala Tyr Trp Gly Ile Asp Glu
                100                 105                 110

Ala Arg Met Asp Cys Arg Cys Leu Arg Arg Met Arg Arg Arg Glu Glu
            115                 120                 125

Glu Ala Ala Glu Ala Arg Ala Gly Pro Thr Glu Arg Gly Ala Gln Gly
        130                 135                 140

Ser Pro Ala Arg Ala Leu Gly Pro Arg Gly Arg Leu Gln
145                 150                 155
```

<210> SEQ ID NO 7
<211> LENGTH: 392
<212> TYPE: DNA
<213> ORGANISM: Mouse
<220> FEATURE:
<221> NAME/KEY: CDS
<222> LOCATION: (1)..(162)
<223> OTHER INFORMATION: Mouse Kv6.2 (3' region)

<400> SEQUENCE: 7

```
gag ctc aag gag cag caa cag cgc gcg gcc agc cct gaa ccg gcc ctg      48
Glu Leu Lys Glu Gln Gln Gln Arg Ala Ala Ser Pro Glu Pro Ala Leu
 1               5                  10                  15 cgc gag gac agc acg cgt gat gac agt aca cgt tcg gcc agc gcc act      96
Arg Glu Asp Ser Thr Arg Asp Asp Ser Thr Arg Ser Ala Ser Ala Thr
                20                  25                  30 gag gac agc tct cag gac cct gag acc gca ggc gcg gca ggg aac ttg     144
Glu Asp Ser Ser Gln Asp Pro Glu Thr Ala Gly Ala Ala Gly Asn Leu
             35                  40                  45 ccg ggc cgg gtg gga ccc tgagctgtac tgagaacttc aagagagtca             192
Pro Gly Arg Val Gly Pro
         50 agagcctcgg aggacaccta gcgccaactg acccaggagt tggcaaactt ggtctggcat    252 atccttgcag ctggctcgcc tccccaagca attcccgagc ttcgcatagc ctggaggata    312 tagcaacctg ctttcttttt tgcttttatt ttcccttcag ttttaaattt tctatggcta    372 attaaaaata attgagtccc                                                392
```

<210> SEQ ID NO 8
<211> LENGTH: 54
<212> TYPE: PRT

```
<213> ORGANISM: Mouse

<400> SEQUENCE: 8

Glu Leu Lys Glu Gln Gln Gln Arg Ala Ala Ser Pro Glu Pro Ala Leu
 1               5                  10                  15

Arg Glu Asp Ser Thr Arg Asp Asp Ser Thr Arg Ser Ala Ser Ala Thr
            20                  25                  30

Glu Asp Ser Ser Gln Asp Pro Glu Thr Ala Gly Ala Ala Gly Asn Leu
        35                  40                  45

Pro Gly Arg Val Gly Pro
    50

<210> SEQ ID NO 9
<211> LENGTH: 22
<212> TYPE: RNA
<213> ORGANISM: Homo sapiens
<220> FEATURE:
<221> NAME/KEY: misc_RNA
<222> LOCATION: (1)..(22)
<223> OTHER INFORMATION: intron/exon transition
<221> NAME/KEY: CDS
<222> LOCATION: (1)..(15)
<223> OTHER INFORMATION: coding region/exon

<400> SEQUENCE: 9 gcc gag gag gag cgg gugagcg                                        22
Ala Glu Glu Glu Arg
 1               5

<210> SEQ ID NO 10
<211> LENGTH: 5
<212> TYPE: PRT
<213> ORGANISM: Homo sapiens

<400> SEQUENCE: 10

Ala Glu Glu Glu Arg
 1               5

<210> SEQ ID NO 11
<211> LENGTH: 36
<212> TYPE: RNA
<213> ORGANISM: Homo sapiens
<220> FEATURE:
<221> NAME/KEY: misc_RNA
<222> LOCATION: (1)..(36)
<223> OTHER INFORMATION: intron/exon transition
<221> NAME/KEY: CDS
<222> LOCATION: (25)..(36)
<223> OTHER INFORMATION: coding region/exon

<400> SEQUENCE: 11
ccccgugucc ccucuccccc gcag ggc gag ugc ucc                         36
                          Gly Glu Cys Ser
                           1

<210> SEQ ID NO 12
<211> LENGTH: 4
<212> TYPE: PRT
<213> ORGANISM: Homo sapiens

<400> SEQUENCE: 12

Gly Glu Cys Ser
 1

<210> SEQ ID NO 13
<211> LENGTH: 27
```

```
<212> TYPE: RNA
<213> ORGANISM: Mouse
<220> FEATURE:
<221> NAME/KEY: CDS
<222> LOCATION: (1)..(27)
<223> OTHER INFORMATION: coding region: transition from exon 1 to exon 2

<400> SEQUENCE: 13 gca gaa gag gaa cgg ggc gag ugc ucc                                    27
Ala Glu Glu Glu Arg Gly Glu Cys Ser
 1               5

<210> SEQ ID NO 14
<211> LENGTH: 9
<212> TYPE: PRT
<213> ORGANISM: Mouse

<400> SEQUENCE: 14

Ala Glu Glu Glu Arg Gly Glu Cys Ser
 1               5

<210> SEQ ID NO 15
<211> LENGTH: 27
<212> TYPE: RNA
<213> ORGANISM: Homo sapiens
<220> FEATURE:
<221> NAME/KEY: CDS
<222> LOCATION: (1)..(27)
<223> OTHER INFORMATION: coding region: transition from exon 1 to exon 2

<400> SEQUENCE: 15 gcc gag gag gag cgg ggc gag ugc ucc                                    27
Ala Glu Glu Glu Arg Gly Glu Cys Ser
 1               5

<210> SEQ ID NO 16
<211> LENGTH: 9
<212> TYPE: PRT
<213> ORGANISM: Homo sapiens

<400> SEQUENCE: 16

Ala Glu Glu Glu Arg Gly Glu Cys Ser
 1               5

<210> SEQ ID NO 17
<211> LENGTH: 32
<212> TYPE: DNA
<213> ORGANISM: artificial sequence
<220> FEATURE:
<223> OTHER INFORMATION: description of the artificial sequence: SEAM 1;
      PCR primer
<221> NAME/KEY: CDS
<222> LOCATION: (18)..(32)
<223> OTHER INFORMATION: Coding region in primer

<400> SEQUENCE: 17
agttactctt caccacc atg gag cca tgg ccc                                 32
                  Met Glu Pro Trp Pro
                   1               5

<210> SEQ ID NO 18
<211> LENGTH: 5
<212> TYPE: PRT
<213> ORGANISM: artificial sequence
<220> FEATURE:
<223> OTHER INFORMATION: Coding region in primer

<400> SEQUENCE: 18
```

```
Met Glu Pro Trp Pro
  1               5
```

<210> SEQ ID NO 19
<211> LENGTH: 32
<212> TYPE: DNA
<213> ORGANISM: artificial sequence
<220> FEATURE:
<223> OTHER INFORMATION: description of the artificial sequence: SEAM 6;
      PCR primer

<400> SEQUENCE: 19
agttactctt caccccgctc ctcctcggcg cg                             32

<210> SEQ ID NO 20
<211> LENGTH: 30
<212> TYPE: DNA
<213> ORGANISM: artificial sequence
<220> FEATURE:
<223> OTHER INFORMATION: description of the artificial sequence: SEAM 5;
      PCR primer
<221> NAME/KEY: CDS
<222> LOCATION: (13)..(30)
<223> OTHER INFORMATION: coding region in primer

<400> SEQUENCE: 20

```
agttactctt ca ggg cga gtg ctc ccc caa                          30
              Gly Glu Cys Ser Pro Lys
                1               5
```

<210> SEQ ID NO 21
<211> LENGTH: 6
<212> TYPE: PRT
<213> ORGANISM: artificial sequence
<220> FEATURE:
<223> OTHER INFORMATION: coding region in primer

<400> SEQUENCE: 21

```
Gly Glu Cys Ser Pro Lys
  1               5
```

<210> SEQ ID NO 22
<211> LENGTH: 27
<212> TYPE: DNA
<213> ORGANISM: artificial sequence
<220> FEATURE:
<223> OTHER INFORMATION: description of the artificial sequence: SEAM 4;
      PCR primer

<400> SEQUENCE: 22
agttactctt catgtgggcg gcgcagg                                   27

<210> SEQ ID NO 23
<211> LENGTH: 17
<212> TYPE: DNA
<213> ORGANISM: artificial sequence
<220> FEATURE:
<223> OTHER INFORMATION: description of the artificial sequence: M13;
      sequencing primer

<400> SEQUENCE: 23
gtaaaacgac ggccagt                                              17

<210> SEQ ID NO 24
<211> LENGTH: 19
<212> TYPE: DNA
<213> ORGANISM: artificial sequence
<220> FEATURE:

-continued

<223> OTHER INFORMATION: description of the artificial sequence:
     reverse; sequencing primer

<400> SEQUENCE: 24
ggaaacagct atgaccatg                                            19

<210> SEQ ID NO 25
<211> LENGTH: 20
<212> TYPE: DNA
<213> ORGANISM: artificial sequence
<220> FEATURE:
<223> OTHER INFORMATION: description of the artificial sequence: T3;
     sequencing primer

<400> SEQUENCE: 25
aattaaccct cactaaaggg                                           20

<210> SEQ ID NO 26
<211> LENGTH: 19
<212> TYPE: DNA
<213> ORGANISM: artificial sequence
<220> FEATURE:
<223> OTHER INFORMATION: description of the artificial sequence: T7;
     sequencing primer

<400> SEQUENCE: 26
ggaaacagct atgaccatg                                            19

<210> SEQ ID NO 27
<211> LENGTH: 5
<212> TYPE: DNA
<213> ORGANISM: artificial sequence
<220> FEATURE:
<223> OTHER INFORMATION: description of the artificial sequence: Kozak;
     for fitting-in into Seam 1

<400> SEQUENCE: 27 ccacc                                                            5

<210> SEQ ID NO 28
<211> LENGTH: 518
<212> TYPE: PRT
<213> ORGANISM: CHICKEN

<400> SEQUENCE: 28

Met Ala Leu Leu Thr Gly Asn Ala Asp Arg Ala Phe Ser Ser Tyr Ser
 1               5                  10                  15

Phe Asn Lys Leu Glu Asn Leu Cys Glu Val Gln Thr Lys Lys Gly Phe
             20                  25                  30

Phe Tyr Arg Lys Ala Lys Leu Leu His Pro Asp Glu Asp Leu Cys Tyr
         35                  40                  45

Leu Ala Arg Leu Asp Asp Arg Thr Arg Phe Val Ile Ile Asn Val Gly
     50                  55                  60

Gly Ile Lys Tyr Lys Val Pro Trp Thr Thr Leu Glu Asn Cys Pro Leu
 65                  70                  75                  80

Thr Arg Leu Gly Lys Leu Lys Ser Cys Asn Asn Tyr Asp Glu Ile Met
                 85                  90                  95

Asn Ile Cys Asp Asp Tyr Asp Val Ser Cys Asn Glu Phe Phe Phe Asp
            100                 105                 110

Arg Asn Pro Ser Ala Phe Arg Thr Ile Met Thr Phe Leu Thr Ala Gly
        115                 120                 125

Lys Leu Arg Leu Leu Arg Glu Met Cys Ala Leu Ser Phe Gln Glu Glu

-continued

```
            130                 135                 140
Leu Val Tyr Trp Gly Ile Glu Glu Asp His Leu Glu Trp Cys Cys Lys
145                 150                 155                 160

Lys Arg Leu Gln Gln Lys Glu Glu Ala Ala Glu Ala Arg Met Tyr
                165                 170                 175

Glu Gly Glu Met Met Phe Ser Glu Thr Thr Gln Cys Ala Phe Gln Asp
                180                 185                 190

Asn Asn Trp Leu Ser Leu Cys Met Arg Asn Leu Arg Asp Met Val Glu
                195                 200                 205

Asn Pro His Ser Gly Ile Pro Gly Lys Ile Phe Ala Cys Ile Ser Ile
            210                 215                 220

Ser Phe Val Ala Ile Thr Ala Val Ser Leu Cys Ile Ser Thr Met Pro
225                 230                 235                 240

Asp Val Arg Glu Glu Glu Asp Arg Gly Glu Cys Ser Gln Lys Cys Tyr
                245                 250                 255

Asp Ile Phe Val Leu Glu Thr Val Cys Val Ala Trp Phe Ser Phe Glu
                260                 265                 270

Phe Leu Leu Arg Ser Ile Gln Ala Glu Asn Lys Cys Ala Phe Leu Lys
                275                 280                 285

Thr Pro Leu Asn Ile Ile Asp Ile Leu Ala Ile Leu Pro Phe Tyr Ile
                290                 295                 300

Ser Leu Ile Val Asp Met Ala Ser Thr Lys Asn Ser Ser Lys Pro Gly
305                 310                 315                 320

Gly Gly Ala Gly Asn Lys Tyr Leu Glu Arg Val Gly Leu Val Leu Arg
                325                 330                 335

Phe Leu Arg Ala Leu Arg Ile Leu Tyr Val Met Arg Leu Ala Arg His
                340                 345                 350

Ser Leu Gly Leu Gln Thr Leu Gly Leu Thr Val Arg Arg Cys Thr Arg
                355                 360                 365

Glu Phe Gly Leu Leu Leu Phe Leu Cys Val Ala Met Ala Leu Phe
                370                 375                 380

Ser Pro Leu Val Tyr Leu Ala Glu Ser Glu Leu Gly Ala Lys Gln Glu
385                 390                 395                 400

Phe Thr Ser Ile Pro Thr Ser Tyr Trp Trp Ala Val Ile Ser Met Thr
                405                 410                 415

Thr Val Gly Tyr Gly Asp Met Val Pro Arg Ser Ile Pro Gly Gln Val
                420                 425                 430

Val Ala Leu Ser Ser Ile Leu Ser Gly Ile Leu Leu Met Ala Phe Pro
                435                 440                 445

Val Thr Ser Ile Phe His Thr Phe Ser Arg Ser Tyr Ser Glu Leu Lys
                450                 455                 460

Glu Gln Gln Gln Arg Ala Ala Ser Arg Gln Met His Gln Leu Glu Glu
465                 470                 475                 480

Ser Thr Lys Leu Ala Gly Gly Ser Ser Gln Trp Ile Thr Ala Ala
                485                 490                 495

Ser Pro Pro Asp Ala Ala Arg Glu Asp Gly Arg Pro Glu Leu Asp Gln
                500                 505                 510

Glu Ala Lys Arg Ser Cys
                515
```

VOLTAGE-GATED POTASSIUM CHANNEL AND ITS USE FOR DEVELOPMENT OF THERAPEUTICS

The present application is a 371 U.S. national phase of PCT/EP99/05983, filed 8 Aug. 1999, which designated the U.S., the entire contents of which is incorporated herein by reference.

The object of the invention is a new voltage-gated potassium channel protein, Kv6.2 (SEQ ID No. 2 and 4). Within the framework of the present invention, heterologous potassium channels are also made available for the first time, containing the potassium channel protein as well as further potassium channel subunits, such as the Kv2.1 protein. According to the invention, vectors are also included, which contain the potassium channel subunit Kv6.2, as well as host cells containing these vectors, and expressing the potassium channel subunit and/or the potassium channels. A further object of the invention is antibodies directed against the potassium channel subunit. Also made available for the first time is a method for the identification of substances which can open, close, activate and inactivate the potassium channels, or modify their biophysical properties. According to one special embodiment of the invention, the method is used for the identification and/or discovery of anti-arrhythmics.

The membranes of mammal cells are very important to the structural integrity and activity of cells and tissue. A number of metabolic processes are controlled by membrane-spanning ion channels. In the past it was possible to identify various ion channels, through which calcium, sodium and/or potassium can pass the cell membrane.

The activity of potassium channels can be regulated either by intra-cellular signal substances such as cAMP or by differences in potential on the cell membrane. These differences in potential or voltages are produced by different ion concentrations inside and outside the cell.

Voltage-gated potassium channels are open or closed depending on the potential present along the cell membrane. Different classes of voltage-gated potassium channels are known, which are as a rule similar in structure. Basically these consist of four homologous α-subunits and four β-subunits. The β-subunits are important for the regulation of the channel's activity, whilst the α-subunits form the actual functional potassium channel (O. Pongs, *Biospektrum* 3 (1997) 21–26). The α-subunits belong to a shared gene super-family. They possess a comparable two-dimensional structure, yielding a membrane topology typical of potassium channels (O. Pongs, *Physiol. Rev.* 72 (1992) 69–88.; L. Y. Jan et al., *Nature* 371 (1994) 119–122; K. G. Chandy et al., in *Handboook of Receptors and Channels* ed. R. A. North, Boca Raton 1 (1994) 1–71). Each α-subunit possesses six hydrophobic membrane-spanning segments S1–S6 and between S5 and S6 the "P-domain" which dips into the membrane from the extracellular side. The e-domain plays a decisive part in the formation of the potassium channel pore. The S4 segment contains several amino acids with positive charges, which probably make an essential contribution to the voltage-sensitivity of the channel.

The family of voltage-gated potassium channel subunits can be divided into several subfamilies, of which the Kv1 to Kv4 families have been well characterized. (W. Stühmer et al., *EMBO J.* 8 (1989) 3235–3244; B. Albrecht et al., *Receptor and Channel* 1 (1993) 99–100; J. Rettig et al., *EMBO J.* 11 (1992) 2473–2486; Serodio et al., *J. Neurphysiol.* 75 (1996) 2174–2179). Within the subfamilies the sequence identity shared by the individual α-subunits lies at the level of the amino acids at ≧60%. The α-subunits of the families Kv1–Kv4 cloned thus far express functional potassium channels in heterologous expression systems, i.e. after injection of DNA and mRNA into *Xenopus oocytes* and/or into tissue culture cells (Chinese Hamster Ovary (CHO) cells, human epithelial kidney (HEK) 293 cells) or after transfection of tissue culture cells with DNA encoding α-subunits in suitable expression vectors such as pcDNA3 (see below).

In addition to α-subunits of Kv1 to Kv4 further potential Kv α-subunits are known (M. A. Post et al., *FEBS* 399 (1996) 177–182; J. P. Hugnot et al., *EMBO* 15 (1996) 3322–3331; A. Castellano et al., *J. Neurosci.* 17 (1997) 4652–4661; J. A. Drewe et al., *J. Neurosci.* 12 (1992) 538–548) which show a Kv1 to Kv4 sequence identity of <60% relative to the amino acids. These channels have been designated Kv5.1, Kv6.1, Kv7.1 and Kv8.1. The main feature of these α-subunits is that although they contain sequence characteristics typical of potassium channel α-subunits, they form no functional channels as homomultimers α-subunits in heterologous expression systems. However it is possible that these α-subunits, together with α-subunits of the Kv2 family, form heteromultimers which are functionally expressible, i.e. they form functional potassium channels (M. A. Post et al (loc. cit.); J. P. Hugnot et al. (loc. cit.); A. Castellano et al. (loc. cit.).

Voltage-gated potassion channels may take over various physiological tasks, ranging from regulation of the membrane rest potential to regulation of exocytosis and cell proliferation. In excitable cells, voltage-gated potassium channels have considerable significance for the repolarization of the action potentials and the regulation of the threshold value, from which an action potential can be released. To this extent the activity of potassium channels controls both the duration and development of the action potential and also the action potential release frequency. This also applies to the rhythmic production of action potentials in the heart muscle tissue, the myocardium (R. E. Ten Eick et al., *FASEB J.* 6 (1992) 2568–2580).

Several distinct potassium channel types are involved in the generation and repolarization of the action potentials in the myocardium. The currents generated by these channels are designated $I_{\tau O}$, $I_{KR}$ and $I_{SK}$. $I_{\tau O}$ is a rapidly activating transient potassium outward current, $I_{ER}$ is a rapidly activating, not inactivating potassium outward current, $I_{SK}$ is a slowly activating potassium outward current. These currents are measured on dissociated myocardium cells kept in culture (R. C. Kass and L. C. Freeman, *Trends Cardiovasc. Med* 3 (1993) 149–159; D. M. Barry and J. M. Nerbonne, *Ann. Rev. Physiol.* 58 (1996) 363–394). The analysis of serious arrhythmias, which lead to a long QT syndrome, i.e. a delayed repolarization of the cardiac action potential, has shown that the $I_{SK}$ current is essentially mediated through KvLQT1/Kv channels (M. C. Sanguinetti et al., *Nature* 384 (1996) 80–83; J. Berhamin et al., *Nature* 384 (1996) 78–80. HERG/Kv channels mediate currents which contribute to the subsequent hyperpolarization and hence to the stabilization of the threshold value (P. L. Smith et al., *Nature* 379 (1996) 833–836). Pharmacologically it is possible to block HERG channels relatively specifically by means of drugs such as E-4031 (P. S. Spector et al., *Cir. Res.* 78 (1996) 499–503). Presumably channels of the types Kv1-5 and Kv4.3 as well as the channels Kv2.1/Kv6.2 channels described here are involved in the formation of the $I_{\tau O}$ and $I_{KR}$ (cf. R. C. Kass and L. C. Freeman, *Trends Cardiovasc. Med.* 3 (1993) 149–159; D. M. Barry and J. M. Nerbourne, *Ann. Rev. Physiol.* 58 (1996) 363–394. It is not yet known, which and how many potassium channels in all are involved in the repolarization of the cardiac action potential.

At present arrhythmias are frequently treated with ion channel blockers. The action of these blockers can be classified according to whether they delay the depolarization speed (increase) of the cardiac action potential (e.g. Flecainid, Phenytoin) or extend the duration of the cardiac action potential (e.g Sotalol, Aminodaron, Chinidin, Disopyramid) or reduce the duration of the cardiac action potential (e.g. Lidocain, Mexiletin). One important preparation is the substance Propafenone (Merck-Index XI 7806), which belongs to the Class 1 c antiarrhythmics (H. Honjo et al. *Br. J. Pharmacol.* 97 (1989) 731–738). Propafenone is used in the case of symptomatic tachycardiac supraventricular arrhythmias requiring treatment, such as AV junctional tachycardia, supraventricular tachicardia in the case of WPW syndrome or paroxysmal atrial fibrillation and serious symptomatic ventricular tachycardiac arrhythmias (J. Braun and R. Preuss Klinikleitfaden Intensivmedizin, 2nd edition, Jung Johann Verlagsgesellschaft, Neckarsulm/Stuttgart (1992)). As described in some experimental works the administration of propafenone, following an occlusion of the heart vessels, leads, to an improved metabolic and functional recovery of the heart (J. X. Liu et al. *Eur. J. Pharmacol.* 250/1 (1993) 361–369).

Propafenone is assumed to act by blocking voltage-gated sodium channels. Propafenone also blocks the L-type calcium channel, a series of potassium channels and β-adrenergic receptors (A. O. Grant *J. Cardiovasc. Elektrophysiol.* 7 (1996) 353–364). At relatively high concentrations, interactions with the individual ion channels and and β-adrenergic receptors are discussed (J. C. Hancox and J. S. Mitcheson. *Br. J. Pharmacol.* 121 (1997) 7–14; B. Koller and M. R. Franz. *J. Cardiovasc. Pharmacol.* 24 (1994) 753–760; G. Malfatta et al. *Eur. Heart J.* 14 (1993) 1253–1257. A channel for which propafenone has a high bonding affinity is however not known in the state of the art.

However propafenone has the disadvantage that the patient may temporarily experience headache, dizziness, flickering in front of the eyes or gastro-intestinal disorders (J. Braun and R. Preuss. Klinikleitfaden Intensivmedizin, 2nd edition, Jung Johann Verlagsgesellschaft, Neckarsulm/Stuttgart (1992). Hypertonic circulation disorders frequently occur in elderly patients. In the case of previous severe damage to the myocardium, undesired impairments of the excitation control in the HIS-Purkinje system and myocardial contractility may occur (P. Vigreux et al. *Therapie* 50 (1995) 413–418; P. J. Podrid and J. L. Anderson. *Am. J. Cardiol.* 15 (1996) 430–434; E. Aliot and I. Denjoy. *Am. J. Cardiol.* 77 (1996) 66A–71A).

Because of the side effects of propafenone and other antiarrhythmics known in the state of the art new active substances are constantly being sought. Specific screening for new antiarrhythmics in the pharmaceuticals industry has to date generally been carried out using Langendorf apparatus, in which the function of an isolated rabbit or mouse heart is measured under either a constant pressure or a constant flow (A. Bethmann et al. *Am. J. Respir. Crit. Care Med.* 153 (1996) A529).

The aim of the present invention is therefore to make available a new test system (assay) that is suitable for testing substances for suitability as antiarrhythmics, i.e. which can be used to test whether active substances are suitable as antiarrhythmics. In particular the assay is to be used to test specific active substances, by a simple method, to determine whether they enable the modulation of $I_{KR}$ currents. With this test system drugs are thus to be tested for their effect on $I_{KR}$ currents. In particular it is the aim of the present invention to provide a test system that makes the use of Langendorf apparatus, which has been necessary up to now, superfluous, or at least strongly restricts it.

According to the invention this task is solved by host cells which express the voltage-gated potassium channel Kv2.1/Kv6.2.

Within the framework of the present invention a new subunit of a potassium channel protein, Kv6.2, is surprisingly made available, which in conjunction with Kv2.1 subunits mediates non-inactivating potassium outward currents, which, because of their properties, may make a contribution to $I_{KR}$ currents. Within the framework of the present invention it emerged that the Kv2.1/Kv6.2 channels according to the invention are highly sensitive to the Class IC antiarrhythmic propafenone. The potassium channels according to the invention are especially suitable for specific identification and development of active substances for the treatment of diseases of the heart circulation system and the nervous system in humans and animals, especially antiarrhythmics.

The human potassium channel protein according to the invention has the amino acid sequence shown in SEQ ID NO: 2.

The murine potassium channel protein according to the invention has the amino acid sequence shown in SEQ ID NO: 4.

According to the invention homologues are also included, i.e. potassium channel proteins of the Kv6.2 type expressed in the myocardium with at least 60% sequence identity, and derivatives or fragments of the potassium channel proteines, that have the same electrophysiological, pharmacological and biological effectiveness and/or immunogenity.

Surprisingly it was ascertained that the to date unknown potassium channel subunit Kv6.2 is prominently expressed in the atrium of the heart of mammals (see example 7). In Northern blots of MRNA extracted from various human tissues, Kv6.2 MRNA was in addition also found in liver, skeletal muscle, kidneys, pancreas, and in very small quantities in brain, lung and placenta.

The potassium channel protein according to the invention, as well as homologues, derivatives or fragments thereof with the same electrophysiological, pharmacological and/or biological effectiveness and/or immunogenity, can be obtained in different ways known to the skilled artisan. On the one hand the potassium channel protein or homologues, derivatives or fragments thereof can be produced by means of chemical synthesis. In addition, antibodies against fragments of the polypeptide can be produced by methods known to the expert (E. Harlow and D. Lane, Antibodies: A Laboratory Manual (1988) Cold Spring Harbor Laboratory, Cold Spring Harbor, N.Y.). By means of these antibodies the potassium channel protein according to the invention or derivatives and fragments thereof can be isolated from cells which express it. These may be cells that naturally express the potassium channel protein, but it is also conceivable that cells can be used, into which coding nucleic acid molecules for the potassium channel protein according to the invention are introduced, and which then express the protein under suitable conditions.

A further object of the invention is a potassium channel, which is characterized in that it contains at least one potassium channel subunit Kv6.2. According to the invention the potassium channel can, in addition to the subunit Kv6.2, also contain other potassium channel subunits, especially the subunits Kv2.1, Kv2.2 and Kv2.3. Especially preferably it additionally contains the potassium channel subunit Kv2.1. The specific properties of the potassium channel depend on the potassium channel subunits that it contains besides Kv6.2. If, besides Kv6.2, it contains the potassium channel subunit Kv2.1, this is a voltage-gated potassium channel which mediates outward currents, given depolarization of the membrane.

A further object of the invention is nucleic acid molecules which are characterized in that they encode the potassium channel proteins and potassium channels according to the invention, their homologues, derivatives and/or fragments with the same electrophysiological, pharmacological and/or biological effectiveness and immunogenity. These nucleic acid molecules according to the invention can especially preferably be selected from:
  a) the nucleotide sequence indicated in SEQ ID NO: 1
  b) syngeneic or complementary sequences of the sequences according to a), to the extent that they encode proteins and polypeptides with the same electrophysiological, pharmacological and/or biological effectiveness and immunogenity, and
  c) allelic variants and fragments of the sequences according to a) and b).

A further component of the invention is a vector, which is characterized in that it contains one or more of the aforementioned nucleic acid molecules. Suitable vectors are pBluescript KS$^+$ and pBluescript KS$^-$ (Stratagene, La Jolla, Calif., US), but are not restricted to these. According to a preferred embodiment of the invention, the vector is an expression vector. One suitable expression vector is pcDNA3 (Invitrogene, Carlsbad, Calif., US), but the invention is not restricted to this. The nucleic acid molecules according to the invention can be cloned into these vectors according to general known methods (T. Maniatis et al., *Molecular Cloning: A Laboratory Manual* (1982) Cold Spring Harbor Laboratory, Cold Spring Harbor, N.Y., US). According to the invention the expression vectors contain control elements for transcription, transcription start, transcription end, mRNA processing and translation, which are present in active form in the expression systems used according to the invention.

The vectors according to the invention preferably contain sequences which facilitate replication of the nucleic acid molecules according to the invention. Especially preferably they further contain sequences which facilitate integration of the nucleic acid molecules into the genome of a host cell.

A further object of the invention is host cells, which are transformed with the vectors according to the invention. These host cells are especially preferably CHO cells or *Xenopus oocytes*. However other possible host cells include eukaryote cells from the group consisting of COS, HEK 293, NIH-3T3, whilst not being restricted to these. It is significant that the promoter or enhancer sequences are suited to the host cells transformed with the vectors. By this means an increased expression of the polypeptides according to the invention can be ensured.

A further object of the invention is a host cell which is characterized in that, besides the vectors according to the invention, it is also transformed with a further vector, which contains a nucleic acid sequence, which encodes another potassium channel subunit. Especially preferably this nucleic acid sequence encodes the potassium channel subunit Kv2.1 (B. Albrecht et al. *Receptor and Channel* 1 (1993) 99–100). It can however also encode other potassium channel units such as Kv2.2 and Kv2.3.

A further object of the invention is a host cell, which expresses a functional potassium channel, which contains the potassium channel subunit Kv6.2. The host cell according to the invention expresses the functional potassium channel preferably on its surface, but it is equally possible that the functional potassium channel is expressed in intracellular membranes.

Also included in the invention is a method for the identification and testing of substances which are suitable for opening, closing, activating, inactivating, and/or modifying the biophysical properties of, the potassium channels expressed by the host cells according to the invention, by:
  a) measuring the potassium outward current on the host cells according to the invention,
  b) bringing the host cells into contact with a substance to be tested,
  c) once again measuring the potassium outward current on the host cells, the difference between the potassium outward currents before and after addition of the substance determining the activity of the substance. The activity of a substance with regard to its ability to open, close, activate, inactivate, and/or modify the biophysical properties of potassium channels, is higher, the lower the concentration of the substance to be added in order to achieve a change in the potassium outward currents.

Especially preferably the host cells used express the potassium channel according to the invention on their surface. In this way the substances can be identified/tested by measuring the outward current of ions from the cells through the potassium channel according to the invention. The outward current of ions is preferably determined with the 'patch-clamp' method (cf. e.g. O. P. Hamill et al., *Pflügers Arch.* (1981) 85–100) by applying depolarising test potentials.

The present invention also includes using methods well known to the specialist to load the host cells according to the invention with $^{85}$Rb-ions, which can permeate through potassium channels as well as potassium ions. The charged cells can be cultivated in the presence of substances to be tested. Subsequently the influence of the substances on the $^{86}$Rb-outward current of the cells loaded with $^{85}$Rb, can be measured using methods known to the skilled person (R. S. Rogowski et al. *Mol. Pharmacol.* 50 (1996) 1167–1177).

According to the invention a substance is designated an opening substance if, after addition of the substance at a membrane potential, at which no potassium outward currents flow without addition of the substance, potassium outward currents flow.

According to the invention a substance is designated an activating substance if, after addition of the substance, an existing potassium outward current is increased.

According to the invention a substance is designated a closing substance if, after addition of the substance at a membrane potential, at which potassium outward currents flow without addition of the substance, no potassium outward currents flow.

According to the invention a substance is designated a inactivating substance if, after addition of the substance, an existing potassium outward current is reduced, without the potassium outward current coming to a complete standstill.

According to the invention a substance is designated a modifying substance if, after addition of the substance, biophysical properties of the potassium channel, such as voltage-dependency, conductivity, activation time constants, inactivation time constants, switching behaviour, open times or closed times, are modified.

Modifications in the voltage-dependency of the activation lead, according to expectations, at test potentials which produce potassium outward currents, to an increase or decrease in current.

Changes in conductivity also lead to an increase or decrease in the potassium outward currents. Changes in the activation time constants lead to a deceleration or acceleration of the activation of potassium outward currents. Changes in the inactivation time constants and the switching behaviour can lead to an increase or decrease in the outward currents during a test pulse. The same applies if the open times or closed times of the potassium channels to be measured are changed (B. Hille, Ionic Channels of Excitable Membranes, 2nd Edition (1993), Sinauer Associates Inc., Sunderland, Mass., (USA).

According to the invention a substance is also designated a modifying substance, if the cell surface expression of the potassium channel is modified by addition of the substance. A change in the cell surface expression leads to an increase/decrease of the potassium outward currents to be measured.

A further object of the invention is a method for the identification and testing of substances which are suitable for opening, closing, activating, inactivating, or modifying the biophysical properties, of potassium channels by a) measuring the membrane potential on the host cells according to the invention, b) bringing the host cells into contact with a substance, c) once again measuring the membrane potential on the host cells, the difference between the membrane potential before and after addition of the substance determining the activity of the substance. The activity of a substance with regard to its ability to open, close, activate, inactivate, or modify the biophysical properties of, potassium channels, is higher, the lower the concentration of the substance to be used in order to achieve a modification of the membrane potential.

A further object of the invention is a method for the identification and testing of substances which are suitable for opening, closing, activating, inactivating, or modifying the biophysical properties of, potassium channels, by a) measuring the membrane potential and the potassium outward current in the host cells according to the invention, b) bringing the host cells into contact with a substance, c) once again measuring the membrane potential and the potassium outward flow, the differences between the membrane potential and the potassium outward current before and after addition of the substance determining the activity of the substance. The activity of a substance with regard to its ability to open, close, activate, inactivate, or modify its biophysical properties of potassium channels, is the higher, the lower the concentration of the substance to be used in order to achieve a change in the membrane potential and the potassium outward current.

The host cells Xenopus oocytes used in the method according to the invention are especially preferred. According to the invention CHO cells and other tissue culture cells such as COS cells and HEK 293 cells are also preferred, however the choice is not restricted to these, so long as a functional potassium channel can be obtained in the host cells used.

Surprisingly, within the framework of the present invention, it has emerged that functional potassium channels, which contain the potassium channel subunits Kv6.2 and Kv2.1, represent a receptor with a high affinity for propafenone. This means that the method according to the invention, using host cells which express the Kv2.1/Kv6.2 potassium channel, is suitable for discovering and testing new or known substances and active substances, which have an effect on the heart rhythm. The method according to the invention is especially preferred for the discovery and testing of Class IC antiarrythmics.

Thus within the framework of the present invention, it is possible to identify substances which are suitable for opening, closing, activating, inactivating, or modifying the biophysical properties of, the potassium channels according to the invention. Because of the specific localization and function of these channels, their modulators (activating or inactivating) can make treatment possible in different cardiovascular and neuronal spheres or areas.

In the cardiovascular sphere, apart from heart rhythm, the strength of contraction and flow of blood through the heart are also important. Modulators of the potassium channels according to the invention can thus potentially be used in arrhythmia or hypertension therapy as well as in cardioprotection.

In the neuronal sphere, potassium channels play a decisive role in the regulation of the activity of neurones. Modulators of these potassium channels can influence potential learning and memory functions and can be used therapeutically, for example, in the case of neurodegenerative diseases (e.g. epilepsy, ischaemia, stroke, Parkinson's disease and Alzheimer's disease).

Also within the framework of the present invention antibodies are made available, which bind to the isolated potassium channel protein according to the invention or to derivatives or fragments thereof with the same electrobiological, pharmacological and/or biological effectiveness and/or immunogenity. Antibodies are further made available which bind to the potassium channel protein according to the invention, or to derivatives or fragments thereof with the same electrophysiological, pharmacological and/or biological effectiveness and/or immunogenity, the potassium channel protein or the derivatives or fragments thereof with the same electrophysical, pharmacological and/or biological effectiveness and/or immunogenity forming part of a potassium channel and thus being able to have a three-dimensional structure different from that of the isolated potassium channel proteins according to the invention. Methods for the production of antibodies are generally known to the expert (E. Harlow and D. Lane, loc. cit.). The antibodies can be obtained by immunising animals with the potassium channel protein according to the invention, or derivatives or fragments thereof with the same electrophysiological, pharmacological and/or biological effectiveness and/or immunogenity. Polyclonal antibodies are then recovered from the serum of the animals, whilst monoclonal antibodies can be obtained from the excess of hybridoma cells. Hybridoma cells can be obtained by fusing antibody-producing cells with tumour cells (E. Harlow and D. Lane, loc. cit.).

Also included according to the invention are species homologues of the human potassium channel protein Kv6.2 according to the invention, as well as its derivatives and/or fragments with the same immunogenity. The species homologues are distinguished by the fact that they come from humans of different species and have an amino acid identity of at least 60% relative to the human potassium channel protein according to the invention and—as already described above—together with other potassium channel subunits form potassium channels which preferably bind Class IC antiarrhythmica.

Especially preferably the species homologue comes from the mouse and has the amino acid sequence shown in SEQ ID NO: 4.

The invention is explained below by means of examples, sequence protocols and figures.

BRIEF DESCRIPTION OF THE FIGURES

FIGS. 1A–1D

A) Genomic organization of the human Kv6.2 gene

Figure 2:
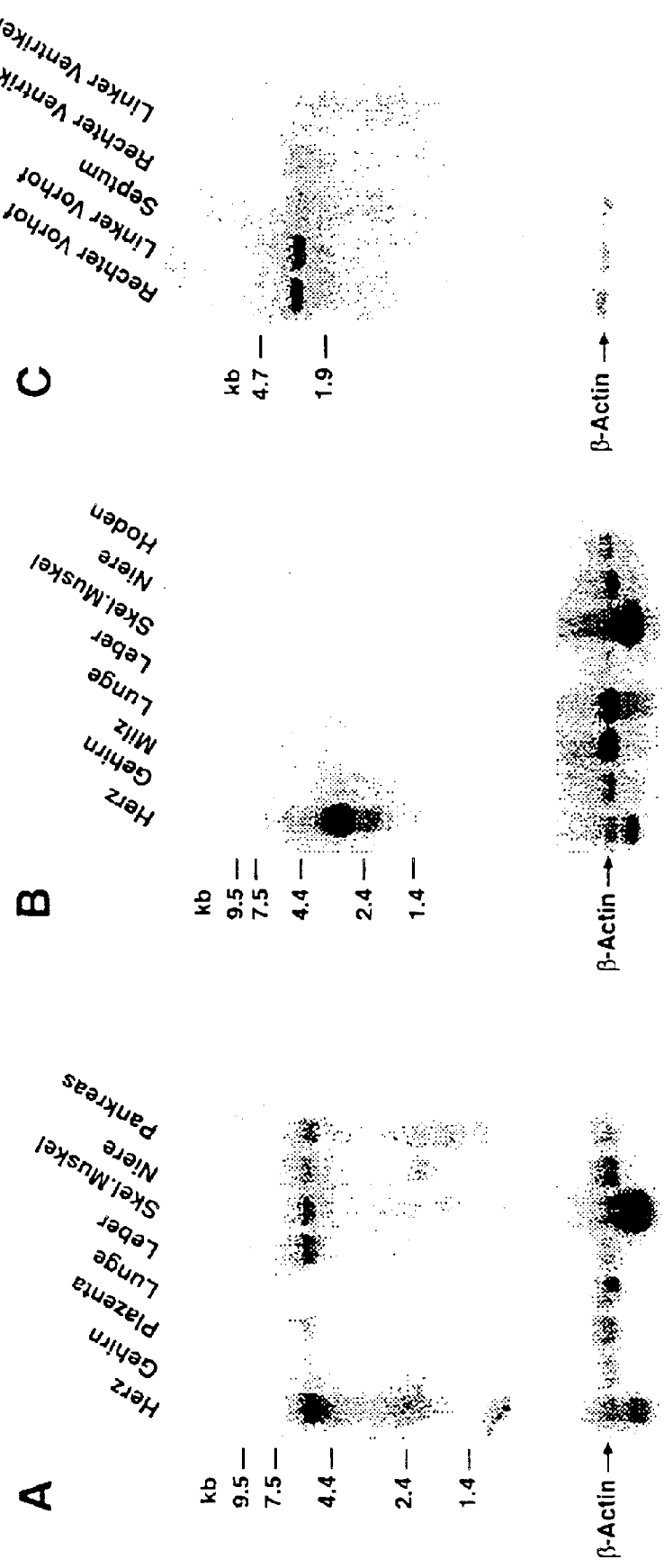

The coding region is schematically represented by two right angles. The seven black bars indicate the six hydrophobic, possibly membrane-spanning segments S1 to S6 and the segment P which is involved in pore formation. Restriction cleavage sites are abbreviated as follows: EV-EcoRV, P-PstI, S-SacI, B-BamHI. These restriction cleavage sites were localized by single/double digestions and sequencing. The exon-intron borders (SEQ ID NO: 9 and 13) were obtained by comparison of the genomic sequence of the human Kv6.2 with the human Kv6.2 cDNA (hKv6.2 CDNA SEQ ID NO: 1) and/or the mouse cDNA (mKv6.2 cDNA SEQ ID NO: 3). The human genomic SacI/PstI fragment (Probe A) was used as hybridization probe for the Northern analysis in FIG. 2. The broken lines refer to the genomic sequences of the exon-intron borders. Intron sequences are underlined. Below the hKv6.2 sequence the derived part-protein sequence is indicated mKv6.2 cDNA and hKv6.2 cDNA show the cDNA sequences in the region of the exon-intron borders.

B-1 and B-2) Conserved nucleotide sequences of the human Kv6.2 (SEQ ID NO: 1) and of the *Mus musculus* Kv6.2 gene (SEQ ID NO: 3) from which the open reading frame was derived.

The dashes (-) in the mouse sequence indicate nucleotides identical to the human sequence.

C) Open reading frame of the derived amino acid sequence(SEQ ID NO: 2) of the human Kv6.2 α-subunit.

The six hydrophobic, possibly membrane-spanning segments are marked S1 to S6. The markings with PKC and CamK show the putative phosphorylation points for protein kinase C and $Ca^{2+}$-calmodulin dependent kinase II.

d) Homology (in %) of the human Kv6.2 protein sequence (SEQ ID NO: 2) to protein sequences of representative members of the individual Kv subfamilies of the rat.

FIGS. 2A–2C

A) Northern analysis of the expression of human Kv6.2 mRNA in different tissues.

The mRNA applied is indicated on top of the lane in question. The human genomic SacI/PstI fragment (SEQ ID NO: 5), which is designated Probe A in FIG. 1, was used as hybridization probe. A Kv6.2 mRNA of 5.5 kb was detected in heart, kidney, muscle, liver and pancreas. The RNA quantity in the individual lanes was checked by hybridization with a labelled β-actin cDNA probe.

B) Northern analysis of the expression of the Kv6.2 mRNA in different rat tissues.

The origin of the mRNA applied is indicated on top of the lane in question. A genomic DNA fragment (SEQ ID NO: 7), which contains the DNA sequence of MKv6.2 between nucleotide 1281–1443 in FIG. 1B was used here as a hybridization probe. An mRNA of 2.6 kb preferentially expressed in the heart was detected. The RNA quantity in the individual lanes was checked by hybridization with a labelled β-actin cDNA probe.

C) Northern analysis of the expression of the Kv6.2 mRNA within different regions of the rat heart.

The mRNAs applied from different regions of the rat heart are indicated on top of the lane in question. The Kv6.2 expression in atria is stronger than in septum and ventricles.

FIGS. 3A–3D

A 393 bp antisense RNA, which represents the nucleotides 1281–1443 of the encoding mKv6.2 DNA (FIG. 1B(b), Seq ID No. 7) was here used for in situ hybridization on sections of adult mouse brain.

A) Preferential expression of the Kv6.2 mRNA in grain cells of Gyrus dentatus and in pyramid cells of the hippocampal CA3 field.

B) Control with a sense-RNA probe.

C) Mouse brain section dyed with the anti-Kv6.2 antibody, with strong coloration being found in the moss fibre system of the hippocampus.

Figure 3:
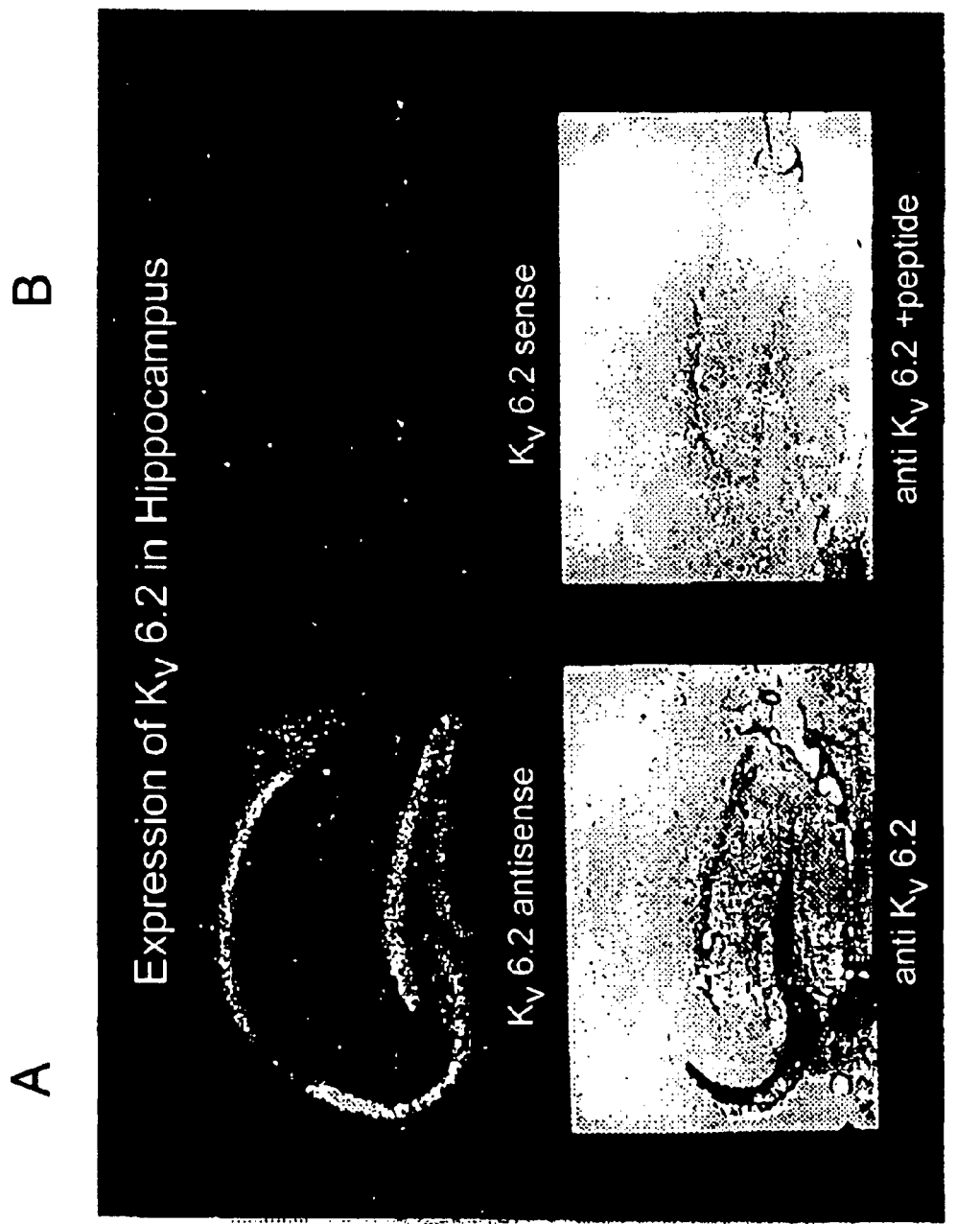
Figure 4:
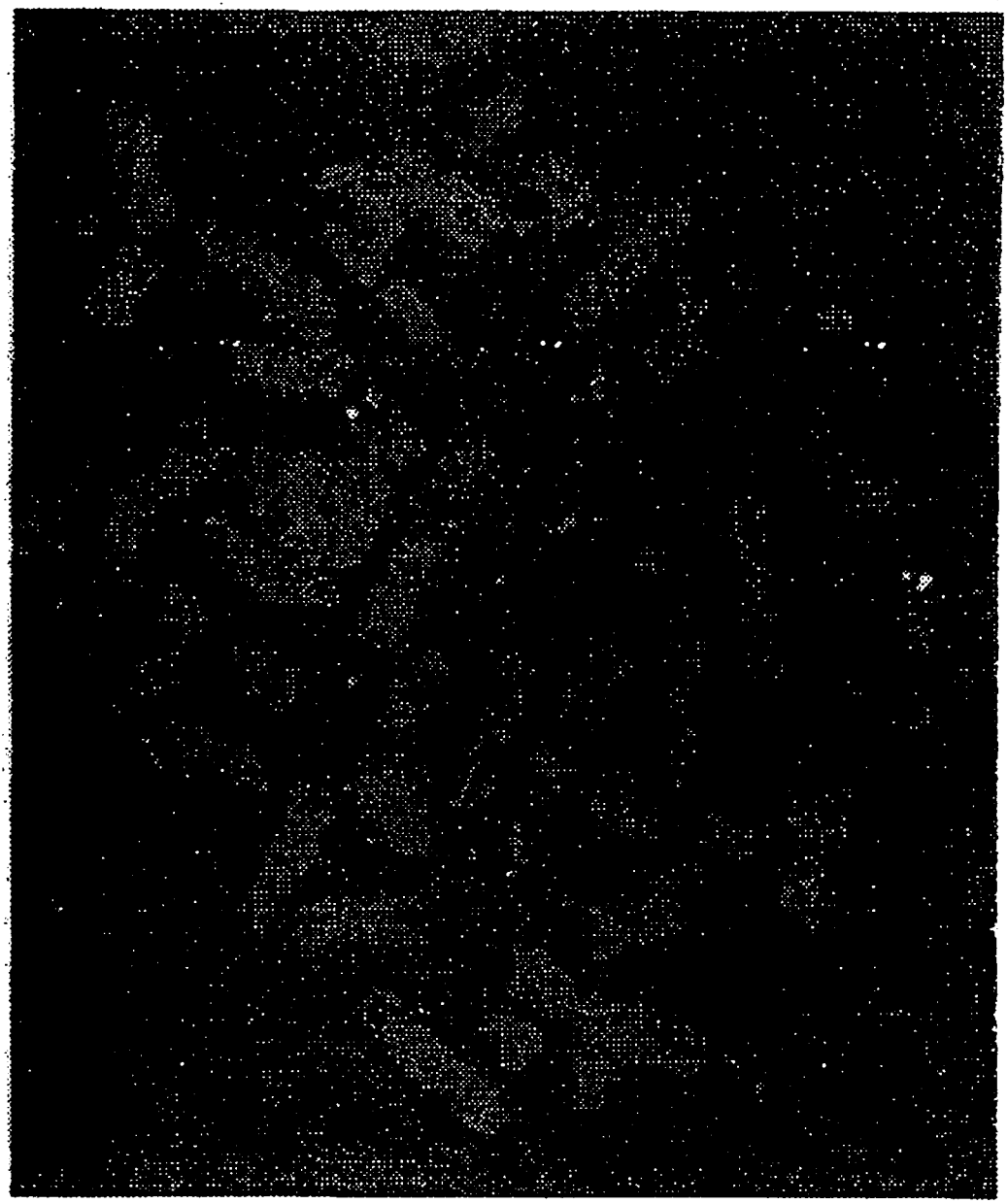
Figure 5:
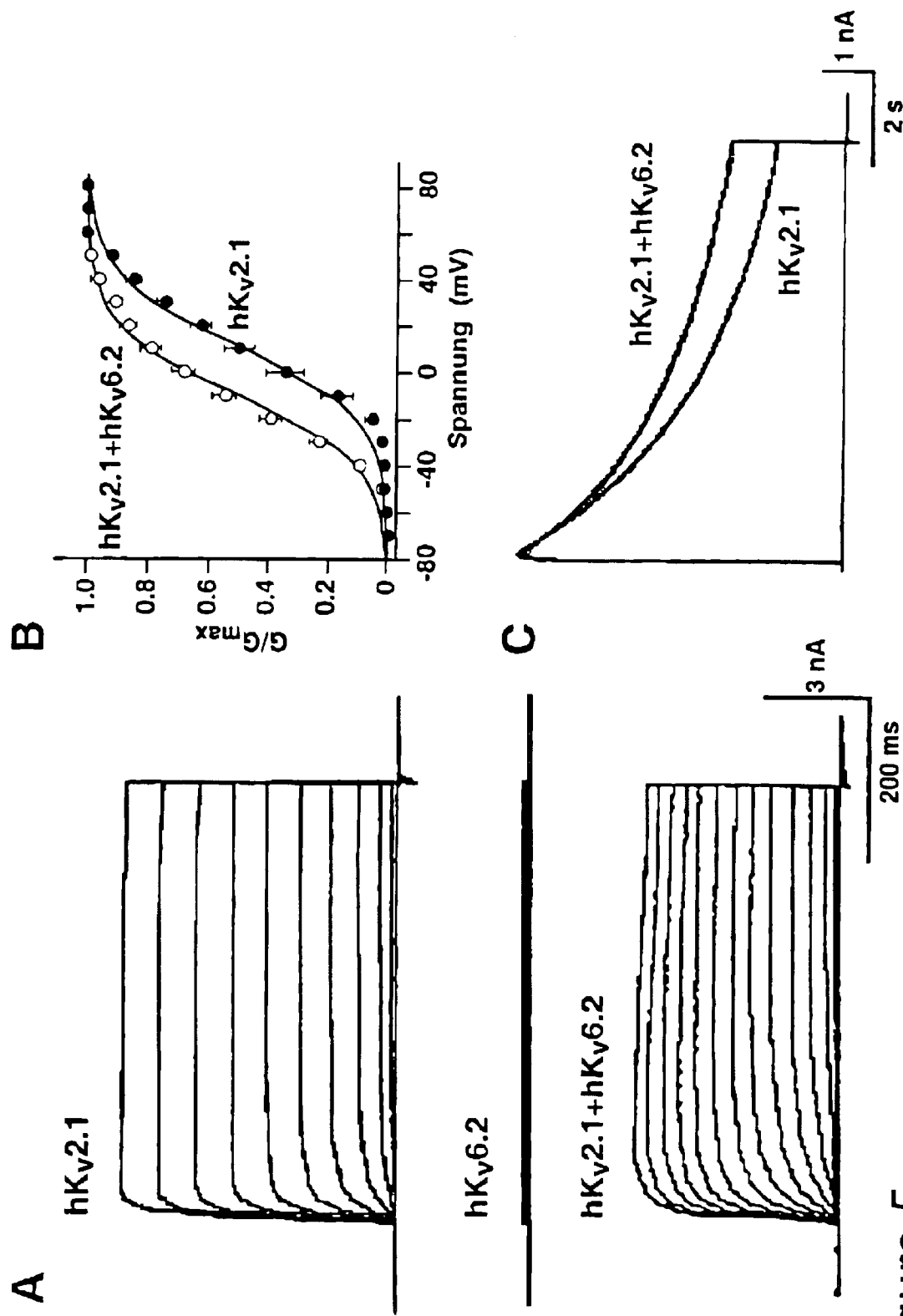

D) Blocking of the coloration shown in FIG. 3C by addition of peptides (Kv6.2 antigen).

FIG. 4

Localization of the potassium channel gene, Kv6.2 in the region of the human chromosome 18q22–23.

FIGS. 5A–5C

Comparison of the kinetic properties of homomultimer Kv2.1 channels with those of channels formed by the coexpression of Kv2.1 and Kv6.2 α-subunits.

A) Outward currents measured using the 'patch-clamp' method on CHO cells transiently transfected with hKv2.1 DNA (B. Albrecht et al., *Receptor and Channels* 1 (1995) 99, EMBL Access. No. L02840) or with hKv6.2 DNA (SEQ ID NO:1) and/or on CHO cells cotransfected with hKv2.1-DNA and hKv6.2-DNA (hKv2.1+hKv6.2)

B) Plotting of normalized conductivities (G/Gmax, ordinates) for human Kv2.1 currents (filled circles) and for coexpressed human Kv2.1 currents with human Kv6.2 (open circles) against the membrane potential (abscissa).

Each point represents the average value±standard error of the measurements carried out in six assays for human Kv2.1 and eleven assays for the Kv2.1–-v6.2 heteromultimers. Unbroken lines represent the equalization curves according to the Boltzmann equation with $V_{0.5}$=+10.8±2.5 mV for Kv2.1 alone and $V_{0.5}$=−10±2.5 mV for currents for Kv2.1 coexpressed with Kv6.2 α-subunits (T test for two groups, p<0.005). There is no difference in the rise between the two curves (S=15.3±1.5 for Kv2.1 homomultimers; S=14.5±9 for Kv2.1/Kv6.2 heteromultimers). The coexpression of hKv2.1 and hKv6.2 shifts the activation voltage curve by 20 mV towards more negative test potentials compared with hKv2.1 alone.

C) Effect of the hKv6.2 α-subunit on the inactivation kinetics of the Kv2.1-mediated outward current.

Figure 6:
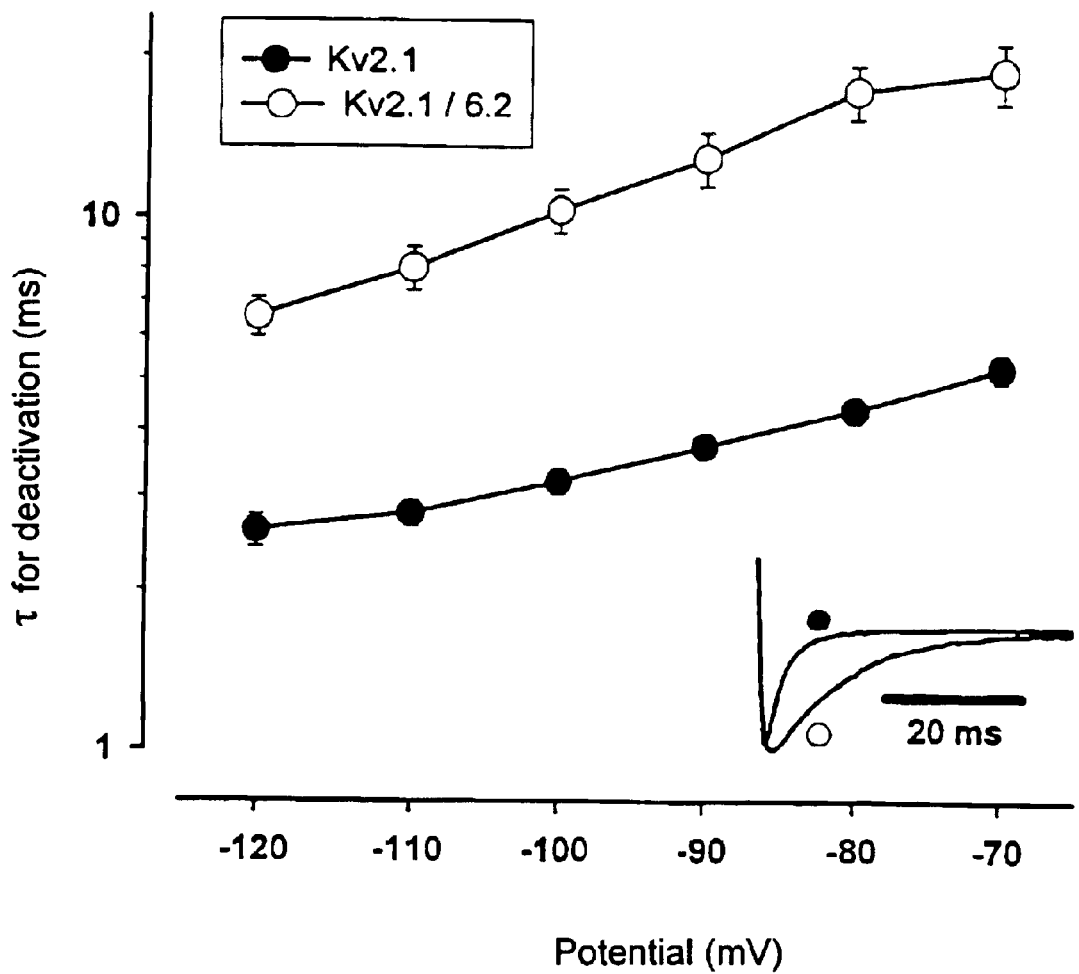
Figure 7:
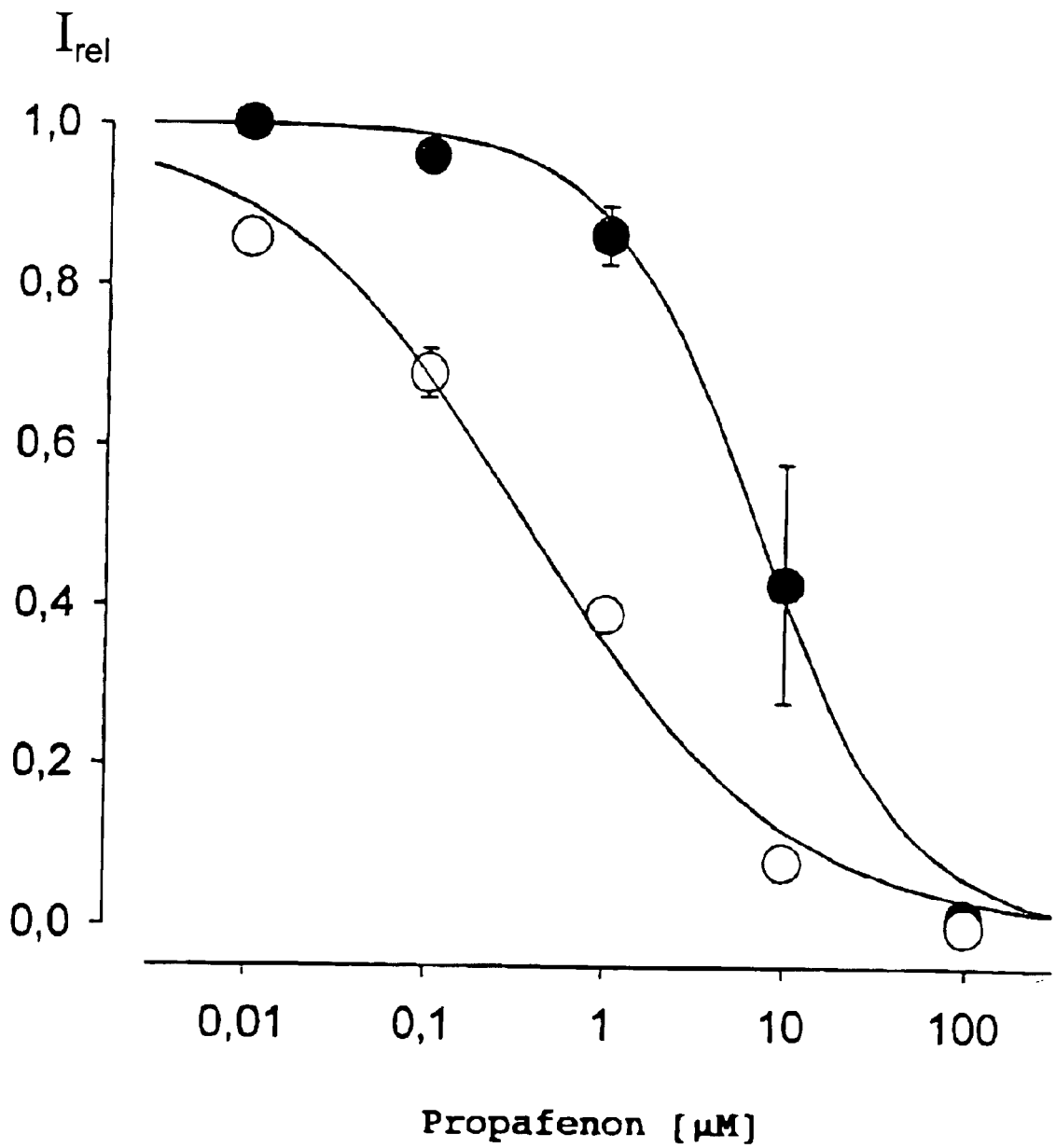

The wave forms of potassium currents in CHO cells, which had been transfected with Kv2.1 alone, were overlaid with those from CHO cells which had been cotransfected with Kv2.1 and Kv6.2 subunits. The depolarization pulses were established at up to +40 mV. The holding potential amounted to −80 mV. The inactivation time constant for Kv2.1 currents amounts to τ=7.17±2.1 msec (n=4), and for Kv2.1/Kv6.2 coexpressed currents it amounts to τ=4.98±5 msec. (n=4). All the transfections were carried out in the presence of the indicator GFP (green fluorescent protein, M. Chalfie et al., *Science* 263 (1994) 802–805, S. Wang and T. Hazelrigg, *Nature* 369 (1994) 400–403). The transfection processes and the conditions for the recording of currents on whole cells were the same as those described in FIG. 6.

FIG. 6

Compared with hKv2.1 the coexpression of hKv2.1 and hKv6.2 shifts the deactivation voltage curve by 60 mV towards more negative test potentials.

FIG. 7

Current-response relations for Kv2.1 and Kv2.1+Kv6.2 mediated currents versus increasing concentrations of propafenone.

EXAMPLES

Example 1

Isolation of Clones from Human and Mouse Genome DNA Libraries $1 \cdot 10^6$ plaques of a SVJ129 mouse genomic DNA library (Clontech, Palo Alto, Calif.) were spread on 20 NZ slides (NZ: 6 g/l NZ powder, 5 g/l yeast extract, 15 g/l bacto-agar; chemicals from Gibco BRL, Eggenstein, DE) with a diameter of 150 mm. The genomic phages DNA was then transferred to 20 membrane filters (Duralon UV membrane, Stratagene). This was followed by hybridization of the filters in 50% formamide, 0.8 M NaCl. 20 mM Pipes (Piperazin-N,N'-bis [2-ethane sulphonic acid], Sigma), 1% SDS, 100 µg/ml denatured herring sperm DNA, in $H_2O$ and with $^{32}P$-labelled mouse Kv3.1 c DNA (nucleotide 223–1356, Access. No. Y07521, Yokoyama et al., 1989) as probe. This hybridization was carried out at 60° C. for 18 hours. The filters were then washed with 0.1×SET/0.1 SDS in $H_2O$ (20×SET: 3 M NaCl, 400 mM Tris/HCl, pH 7.4, 200 mM EDTA; chemicals from Sigma, for 0.1SET, 20×Set is diluted 1:200). Following autoradiography at −70° C. the signals visible on the X-ray films (Kodak, Rochester, N.Y.) were assigned to the corresponding plaques on the slides.

The genomic DNA fragments were isolated from the positive phage clones and then digested with SaxI, XbaI, EcoRI, BamHI and PstI both singly and doubly. The digested DNA fragments were electrophoretically fractionated in an agarose gel and then transferred to nylon membrane. Three digested DNA fragments were identified by a further hybridization, carried out as above. These were a 1.0 kb BamHI/SacI fragment, a 1.0 kb XbaI/SacI fragment and a 0.9 kb SacI/PstI fragment. The sequencing of the three DNA fragments showed that together they contained the whole coding region for Kv6.2.

Figure 1A:
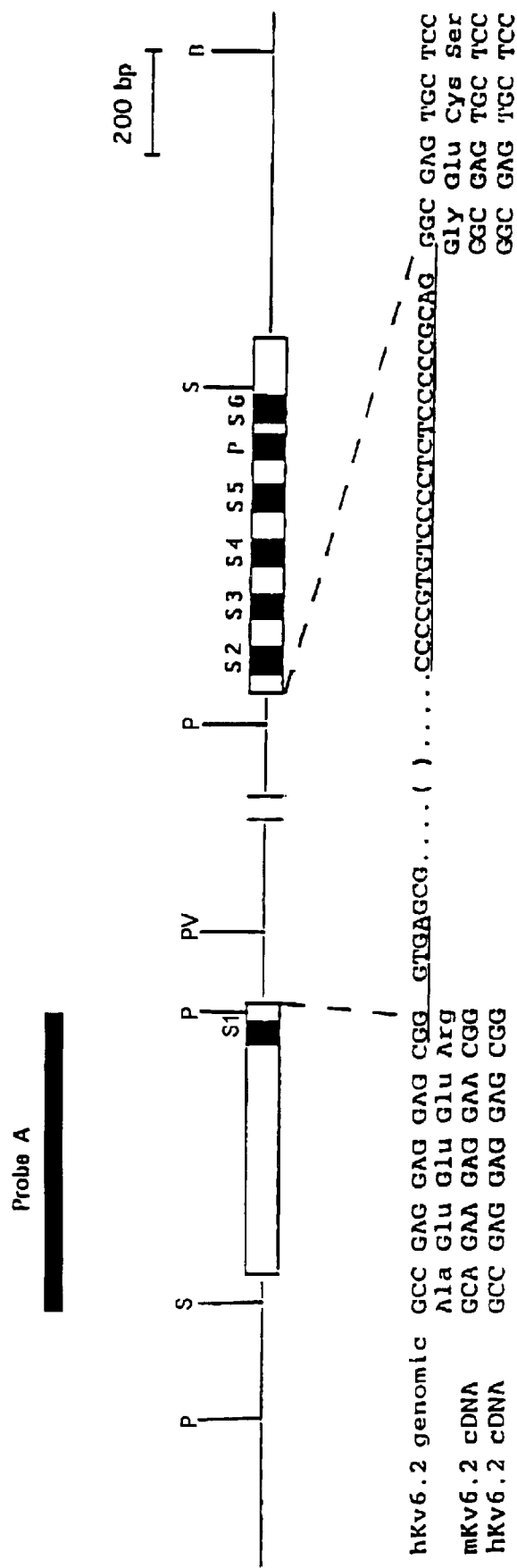

The three isolated genomic mouse DNA fragments were then used for isolation of the human Kv6.2 gene as hybridization probes, with $1 \cdot 10^6$ phage plaques from a human genomic DNA library (Clontech, Palo Alto, Calif.) being spread on slides. The hybridization and washing conditions were as described above. Following Southern analysis and sequencing three human genomic fragments were obtained: a 1.5 kb SacI/EcoRV fragment, a 0.8 kb PstI/SacI fragment and a 0.8 kb SacI/BamHI fragment (FIG. 1A), which together contained the whole coding area for Kv6.2 (FIG. 1C).

Example 2

Mapping of the Restriction Cleavage Sites Within the Isolated Genomic DNA Area To produce a restriction map the insertions of the isolated genomic phage DNAs were singly or doubly digested with restriction enzymes according to standard methods and the fragments were then electrophoretically fractionated in the agarose gels (T. Maniatis et al, loc. cit.). Length comparisons of the digested DNA fragments made it possible to produce the restriction maps of the isolated genomic regions (see FIG. 1A). The DNA fragments, which contain the coding area of the Kv6.2 gene were localized within the isolated genomic regions by Southern analyses, using methods known to the specialist (T. Maniatis et al, loc. cit., E. M. Southern, *J. Mol. Biol.* 98 (1975) 503–517). The sequencing of these DNA fragments made it possible to identify the transcription direction of the Kv6.2 gene.

Example 3

DNA Sequencing

The DNA fragments which corresponded to the coding region of the Kv6.2 gene were cloned into the EcoRI cleavage sites of the Bluescript vector (Stratagene, La Jolla, Calif.). The Kv6.2 DNA was then sequenced according to the method of Sanger et al (*P.N.A.S. USA* 74 (1977) 5463–5467 with T7-DNA polymerase (Sequenase, US Biochemicals, Cleveland, Ohio). Plasmid-specific oligonucleotides M13, reverse, T3 and T7 (Stratagene, La Jolla, Calif., SEQ ID Nos: 23–26) were used as primers for the sequencing.

Example 4

Northern Analysis

The Multiple Tissue Northern (MTN) blot (Clontech, Palo Alto, Calif.) contains 2 mg poly-$A^+$ mRNA from heart, brain, placenta, lung, liver, skeletal muscle, kidney and pancreas respectively. The 0.6 kb SacI/PstI fragment (Probe A in FIG. 1A) was $^{32}P$-labelled (T. Maniatis et al, loc. cit.) and then used as hybridization probe. The probe was hybridized onto the mRNA in hybridising solution (50% formamide, 5×SET, 10× Denhardt's (100× Denhardt's: 20 g/l Ficoll 400 (Sigma), 20 g/l BSA (Sigma), 20 g/l polyvinyl pyrolidone (Merck), diluted 1:10), 1% SDS (Biorad), 100 mg/ml herring sperm DNA (Sigma) in $H_2O$) for 24 hours at 42° C. The blot was then washed successively in washing solution 1 (2×SSC (20×SSC:173 g/l NaCl, 88.2 g/l NaCitrate, pH 7.0, all chemicals from Sigma, for 2×SSC diluted 1:10)); 0.1% SDS: in $H_2O$) at RT and in washing solution 2 (0.1×SSC (20×SSC diluted 1:200); 0.1% SDS; in $H_2O$) at 50° C. After washing autoradiography was carried out on the X-ray films (Kodak, Rochester, N.Y.) at −70° C.

The second Multipe Tissue Northern (MTN) Blot (Clontech, Palo Alto, Calif.) contains 2 mg poly-$A^+$ mRNA from rat heart, brain, spleen, lung, liver, skeletal muscle, kidney and testis respectively. The Northern blot with RNA from rat heart contains 5 mg poly-$A^+$ mRNA from left atrium, right atrium, septum, left ventricle and right ventricle respectively. The 1.2 kg SacI/SacI genomic mouse DNA fragment was $^{32}P$-labelled and then used as hybridization probe for the two blots. The hybridization and washing conditions and the autoradiography conditions corresponded to those of the first MTN blot.

Example 5

PCR

The connection of the two coding regions of the human Kv6.2 gene was carried out by a combination of PCR technology and digestion with the Type IIS restriction endonuclease Eam 1104 (K. A. Padgett et al. *Gene* 168 (1996) 31–35). The first 624 bp coding region for N-terminus and S1-segment (Nucleotides 1–624 of Seq. ID. No. 1) was amplified by PCR with two oligonucleotides Seam1 (SEQ ID NO: 17) and Seam6 (SEQ ID NO: 19), using the 1.2 kb genomic human SacI/EcoRV DNA fragment as a matrix. A Kozak sequence (5'-CCACC-3', SEQ ID NO: 27) was inserted into the Seam1 oligonucleotide before the start codon. The second 777 bp coding region for S2–S6 segments and C terminus (nucleotides 625–1401 of Seq. ID. No. 1) was amplified by a second PCR with Seam5 (SEQ ID NO: 20) and Seam4 (SEQ ID NO: 22) oligonucleotides, using the 1.6 kb PstI/BamHI genomic human DNA fragment (FIG. 1A) as matrix. A total of 14 reaction cycles was carried out for both amplifications with KlenTag polymerase (Clontech, Palo Alto, Calif.), the methylated deoxycytosintriphosphates (dCTPs, Stratagene) being inserted into the DNA fragment by the addition of 5'-methyl-dCTP in the last five reaction cycles. The subsequent digestion with Eam 1104I (Stratagene, La Jolla, Calif.) produced complementary overhanging ends at the 3' end of the first PCR fragment (CCC) and at the 5' end of the second PCR fragment (GGG). The inserted methylated dCTP prevented the digestion of the internal Eam 1104I cleavage sites in the PCR fragments. By ligation with T4-DNA-ligase (MBI Fermentas, Buffalo, N.Y.) the two PCR fragments were connected with each other. This resulted in a DNA fragment with the whole coding region of the human Kv6.2 gene.

Example 6

Human Chromosomal Localization

A 14 kb-long human genomic λDNA clone, which contains the coding region for S2–S6 and C terminus of the Kv6.2 α-subunit, was labelled with Biotin-16-dUTP (Boehringer, Mannheim) and then used as a probe for a FISH analysis. The FISH analysis was carried out according to the method described by P. Lichter et al., *PNASS USA* 85 (1988) 9664–9668 and C. Fonatsch et al., *Int. J. Cancer* 26 (1980) 749–754. The signals were detected with fluorescence-isothiocyanate coupled Avidin-DCS® (Vector Laboratories) and localization of the signals in metaphase chromosomes was carried out using a confocal Laser Scanning microscope (C. Zeiss, LSM 410, Germany).

Example 7

In Situ Hybridization and Immunocytochemistry

The 393 bp-long DNA fragment (nucleotides 1–393 of SEQ ID NO: 7) from the 0.9 kb mouse SacI/PstI DNA fragment was recloned into the Bluescript vector. Two linealized DNA clones with this insertion in two different orientations were used for the syntheses of anti-sense RNA and sense RNA using the mMessagemMachine kit (Ambion, Austin, Tex.), the RNAs being synthesized using $T_3$- and/or $T_7$-RNA-polymerase and labelled with $^{33}$P-UTP (Melton et al., *Nucleic Acids Res.* 12 (1984) 7035–7056).

10–16 µm thick frozen section were prepared in a cryostat and dried at room temperature. The sections were then fixed for 5 min, in ice-cold, PBS-buffered, 4% formalin solution. The hybridization processes with the $^{33}$P-labelled antisense and sense RNAs took place in hybridization solution (50% formamide (Fluka), 10% dextransulphate (Sigma), 0.3 M NaCl (Sigma), 20 mM Tris/HCl (Sigma, pH=7.4), 5 mM EDTA (Sigma), 20 mM DDT (dithiotreitol, Sigma), 1× Denhardt's reagent (100× Denhardt's diluted 1:100) 100 µg/ml denatured salmon sperm DNA, 200 µg/ml yeast tRNA) under a cover glass overnight at 42° C. The sections were then washed in 1×SSC/4 mM DTT at 55–65° C. The slides were then dehydrated using 1×SCC/4 mM DDT, 0.1×SSC, 75% ethanol, and air-dried. Exposure took place for 3–7 days at room temperature with MR film (Kodak, Rochester, N.Y.). The sections were then immersed in photo emulsion (Kodak, Rochester, N.Y.) preheated to 42°, dried overnight at room temperature and exposed at 4° C. for 1 week. Development was carried out with D19 developer and Unifix (Kodak, Rochester, N.Y.).

For production of the antigen peptides, the 393 bp DNA fragment (nucleotides 1–393 of SEQ ID NO: 7) was isolated out of the 0.9 kb genomic SacI/PstI mouse DNA fragment and then recloned into the coding reading frame of the Glutathion-S-Transferase (GST) gene in the pGEX-2T vector (D. B. Smith and K. S. Johnson, *Gene* 67 (1988) 31–40). This DNA fragment contained the coding region for the C terminus of the mKv6.2 α-subunit (C-mKv6.2, SEQ ID NO: 8). The fusion protein of GST and C-mKv6.2 was induced by the addition of 1 mM IPTG (isopropylthiogalactoside, Gibco-BRL) in the *E-coli* bacterial strain XL-1 Blue (Stratagene) transformed with this plasmid DNA and then purified using Glutathion-Agarose (Sigma, St. Louis, Mo.). Two approx. 4–5 month old female rabbits were immunized with this fusion protein according to the standard method (E. Harlow and D. Lane loc. cit.). For the affinity cleaning of the Anti-Kv6.2 antibody C-mKv6.2 was induced with a His-tag in the bacterial strain BL21, which contained the pET-16b vector (Novagen, Madison, Wis., F. W. Studier et al., Methods in Enzymology 185 (1990) 60–89) with the 393 bp DNA fragment (nucleotides 1–393 of Seq. ID. No. 7). The cleaning up of the C-mKv6.2 protein with His-tag was carried out using a nickel column (Novagen, Madison, Wis.). Approx. 100 µg purified C-mKv6.2 protein was bound to a 1 $cm^2$ nitrocellulose membrane (Schleicher & Schuell, Keen, N.H.) and then blocked for two hours with 1×PBS solution with 5% milk powder at room temperature. The membrane obtained was incubated overnight at 4° C. in the PBS solution with rabbit antiserum diluted 1:5, and then washed once in washing solution 1 (1×PBS (20×PBS: 3 M NaCl, 161 mM $Na_2HPO_4$, 39 mM $KH_2PO_4$, diluted 1:20), 1% BSA (Sigma), 0.5% Triton X-100 (Sigma) and twice in washing solution 2 (1×PBS, 1% BSA). The elution took place in an elution solution (0.2 M glycine, 0.15 M NaCl, 0.1% BSA, pH=2.5).

Adult mice were stunned and perfused with a solution of 4% formaldehyde, 0.05% glutaraldehyde and 0.2% picric acid in 0.1 M phosphate buffer (pH=7.4). After fixing, rinsing was carried out with 0.15 M saccharose in 0.13 M phosphate buffer (pH=7.4), the brain was surgically removed and frozen to −50° C. 20 µm thick frozen sections were then prepared at −21° C. The sections were reduced for 30 min at room temperature using 1% $NaBH_4$, and then washed with PBS. To destroy the endogenous peroxidase activity the sections were treated at RT for 30 minutes with 0.05% phenylhydrazine and 10% normal goat serum (Gibco-BRL) with 0.3% Triton x-100. The sections were incubated with the purified Anti-C-mKv6.2 antibody diluted 1:50 overnight at 4° C. For the peptide blocking assay this antibody was preincubated in a 10 µg/ml antigen-peptide solution for 2 hours at room temperature. After washing with PBS the sections were incubated for a further 3 hours at room temperature with the second antibody solution (biotinylated goat-rabbit antibody, 1:2000 in PBS, Camon) and then incubated with the Elite-ABC complex (Vectastain Elite-ABC kit, Vector) for 1 hour at room temperature. The colour reaction with 3,3'-diaminobenzidine was carried out in 0.015% $H_2O_2$ for 3 min (S. M. Hsu et al., *J. Histochem. Cytochem.* 29 (1981) 577–580).

Example 8

Functional Expression and Electrophysiological Technique

The DNA fragment (SEQ ID NO: 1), which contained the whole coding region for the hKv6.2 α-subunit, was cloned into the pCDBA3 vector, which is well known to the skilled artisan (Invitrogene, Carlsbad, Calif.) for expression studies. hKv2.1 cDNA was also inserted into another pCDNA vector (Invitrogene, Carlbad, Calif.). In all, 1 μg plasmid (either Kv2.1 or Kv6.2 alone, or Kv2.1 together with Kv6.2) and 1 μg DNA for GFP were used for transfection of CHO cells with DMRIE-C reagent (a 1:1 mixture of cation-lipid DMRIE and cholesterol, Gibco-BRL, Life Technologies). 500 ml Opti-MEM 1-Medium (Gibco-BRL, Life Technologies) with 2 μg plasmid DNA and 500 ml Opti-MEM 1-Medium with 6.4 μl DMRIE-C reagent were mixed together and then incubated at RT for 45 minutes, forming a liposom-DNA complex. $2 \cdot 10^5$ CHO cells were first washed in a 35 mm dish with Opti-MEM 1-Medium, and the solution with this lipid-DNA complex was then spread out onto the cell layer. After incubation for 5–6 hours at 37° C. in an incubator under 5% $CO_2$ the solution was replaced with normal medium, and the cells were incubated for a further 12–24 hours at 37° C. Subsequently, $5 \cdot 10^4$ cells were transferred into a new dish (35 mm) for the electrophysiological measurements. outward currents were measured 24–48 hours after the transfection using the whole-cell configuration of the patch-clamp technique (O. P. Hamill et al., *Pflügers Arch*. (1981) 85–100). The micropipettes were pulled with a DMZ Universal Puller (Zeitz Instruments, Augsburg, Germany) and had a resistence between 2–3 MΩ after filling with the intracellular solution (105 mM potassium aspartate, 20 mM KCl, 10 mM BAPTA, 10 mM HEPES, 1.5 mM $MgCl_2$, 2 mM $CaCl_2$, 5 mM glucose, 2 mM ATP-$Na_2$, pH=7.2, all chemicals from Sigma). For the electrophysiological measurements the CHO cells were first held in an extracellular solution (140 mM NaCl, 5.3 KCl, 1 mM $MgCl_2$, 2 mM $CaCl_2$, 10 mM HEPES, 5 mM glucose, pH=7.3) at a holding potential of −80 mV and then depolarized at a test potential of −70 to 80 mV at intervals of 10 mV of 300 ms duration each.

What is claimed is:

1. An isolated potassium channel subunit protein comprising the amino acid sequence of SEQ ID NO: 2.

2. An isolated potassium channel subunit protein consisting of the amino acid sequence of SEQ ID NO: 2.

3. An isolated potassium channel comprising the potassium channel subunit protein of claim 1.

4. The potassium channel of claim 3 further comprising a potassium channel subunit protein Kv2.1.

5. The potassium channel of claim 4 wherein said channel has the electrobiological effect of shifting the activation voltage curve by 20 mV towards more negative test potential compared to hKv2.1 alone, and/or by shifting the deactivation voltage curve by 60 mV towards more negative test potential compared to hKv2.1 alone.

6. The potassium channel according to claim 3 which is a voltage-gated potassium channel.

7. An isolated nucleic acid molecule encoding a potassium channel subunit protein of claim 1.

8. An isolated nucleic acid molecule comprising the nucleotide sequence of SEQ ID NO: 1.

9. A vector comprising one or more of the nucleic acid molecules of claim 7.

10. The vector according to of claim 9 further comprising a nucleic acid molecule encoding a potassium channel subunit protein Kv2.1.

11. The vector of claim 9 which is an expression vector.

12. An isolated host cell transformed with a vector of claim 9.

13. An isolated host cell transformed with a vector of claim 10.

14. An isolated host cell transformed with a vector according to claim 9 and a further vector which contains a nucleic acid molecule which encodes a further potassium channel protein, wherein the further potassium channel protein is Kv2.1.

15. The host cell of claim 12, which is a CHO cell.

16. The host cell of claim 12, which is a Xenopus oocyte.

17. The host cell of claim 12, which expresses the potassium channel encoded by the vectors.

18. A method for expression of a potassium channel, comprising culturing a host cell of claim 12 under conditions suitable for the expression of the potassium channel.

19. A method for identification and testing of substances which have the activity of opening, closing, activating, inactivating, or modifying the biophysical properties of potassium channels, comprising a) measuring the potassium outward current on host cells of claim 12, b) contacting the host cells with a substance and c) measuring the potassium outward current on host cells, the difference between the potassium outward current before and after the addition of the substance determining said activity of the substance, and d) inferring from said activity the ability of said substance to open, close, activate, inactivate or modify the biophysical properties of potassium channels.

20. The method of claim 19, wherein the potassium outward current is determined using the 'patch-clamp' method.

21. The method of claim 19, wherein a substance is an opening substance if, after the addition of the substance at a membrane potential at which no potassium outward currents flow without addition of the substance, potassium outward currents flow.

22. The method of claim 19, wherein a substance is an activating substance if, after addition of the substance, an existing potassium outward current is strengthened.

23. The method of claim 19, wherein a substance is a closing substance if, after addition of the substance at a membrane potential at which without addition of the substance potassium outward currents flow, no potassium outward currents flow.

24. The method of claim 19, wherein a substance is an inactivating substance if, after addition of the substance an existing potassium outward current is reduced, without the potassium outward current coming to a complete standstill.

25. The method of claim 19, wherein a substance is a modifying substance if, after addition of the substance, biophysical properties of the potassium channel, such as voltage dependency, conductivity, switching behaviour, open times or closed times, are modified.

* * * * *